US005712272A

United States Patent [19]
Harris et al.

[11] Patent Number: 5,712,272
[45] Date of Patent: Jan. 27, 1998

[54] THERAPEUTIC COMPOSITIONS

[75] Inventors: Gregory David Harris; Marc Jerome Chapdelaine, both of Wilmington, Del.; Paul Francis Jackson, Chadds Ford, Pa.

[73] Assignee: Zeneca Limited, United Kingdom

[21] Appl. No.: 782,279

[22] Filed: Jan. 13, 1997

Related U.S. Application Data

[63] Continuation of Ser. No. 524,557, Sep. 7, 1995, which is a continuation of Ser. No. 74,907, Jun. 10, 1993, Pat. No. 5,492,905.

[30] Foreign Application Priority Data

Jun. 10, 1992 [GB] United Kingdom ............... 9212308

[51] Int. Cl.$^6$ .................... A61K 31/55; C07D 223/16
[52] U.S. Cl. ................................. 514/213; 540/523
[58] Field of Search ............................... 514/213

[56] References Cited

U.S. PATENT DOCUMENTS

| 4,410,520 | 10/1983 | Watthey ................... 424/263 |
| 4,473,575 | 9/1984 | Watthey ................... 424/244 |
| 4,477,446 | 10/1984 | Jones et al. ............... 424/260 |
| 4,575,503 | 3/1986 | Watthey ................... 514/213 |

FOREIGN PATENT DOCUMENTS

| 0 072 352 | 2/1983 | European Pat. Off. ........ 514/213 |
| 0130538A | 1/1985 | European Pat. Off. . |
| 3416695 | 11/1985 | Germany . |
| 49-28753 | 7/1974 | Japan . |
| 49-28754 | 7/1974 | Japan ..................... 514/213 |
| 1 340 334 | 12/1973 | United Kingdom . |
| 2 103 614 | 2/1983 | United Kingdom . |
| WO 9105-549 | 5/1991 | WIPO . |
| WO 92/11854 | 7/1992 | WIPO . |
| WO 94/00124 | 1/1994 | WIPO ..................... 544/353 |

OTHER PUBLICATIONS

Abstract of ZA 8303–903–A (Oct. 1, 1984).
Abstract of EP–107–095.–A (May 2, 1984).
Abstract of AZ 8309–532–A (Jun. 24, 1985).
Abstract of US 3,989,689 (Nov. 2, 1976).
Chemical Abstracts 82:139981g (1975).
Abstract of US 4,477,446 (Oct. 16, 1984).
Abstract of US 3,949,081 (Apr. 6, 1976).
Abstract of US 4,965,356 (Oct. 27, 1990).
Abstract of EP 400–665–A (Dec. 5, 1990).
Abstract of DE 3,416,695 (Nov. 7, 1985).
J. Org. Chem., 40, 3874 (1975).
Can. J. Chem., 52, 610, (1974).
J. Heterocyclic Chem., 26, 793, (1989).
Molecular Pharmacolgy, 41:1130–1141 (1992).
Abstract of EP–166–353–A (Jan. 2, 1986).
Abstract of EP–166–357–A (Jan. 2, 1986).
Abstract of EP–166–354–A (Jan. 2, 1986).
Abstract of US 4,692,522 (Sep. 8, 1987).
Abstract of US 4,757,068 (Jul. 12, 1988).
Abstract of EP–322–779–A (Jul. 5, 1989).

*Primary Examiner*—Robert T. Bond
*Attorney, Agent, or Firm*—Michael D. Alexander

[57] ABSTRACT

Benz[b]azepine compounds, pharmaceutical compositions containing them and methods for the treatment of neurological disorders utilizing them.

7 Claims, No Drawings

THERAPEUTIC COMPOSITIONS

This applications is a continuation of our prior copending application Ser. No. 08/524,557, filed Sep. 7, 1995, which in turn is a continuation of our prior application Ser. No. 08/074,907, filed Jun. 10, 1993, now U.S. Pat. No. 5,492, 905.

This invention relates to benz[b]azepine compounds useful in the treatment of neurological disorders generally in mammals such as man. More specifically, the compounds are useful in the treatment of strokes and/or other neurodegenerative disorders such as hypoglycemia, cerebral palsy, transient cerebral ischemic attack, perinatal asphyxia, epilepsy, psychosis, Huntington's chorea, amyotrophic lateral sclerosis, Alzheimer's disease, Parkinson's disease, Olivo-pontocerebellar atrophy, viral-induced neurodegeneration such as in acquired immunodeficiency syndrome and its associated dementia, anoxia such as from drowning, spinal cord and brain trauma, poisoning by exogenous neurotoxins, and chronic pain, for the prevention of drug and alcohol withdrawal symptoms, and for the inhibition of tolerance and dependence to opiate analgesics. The invention particularly relates to novel benz[b]azepine compounds useful in reducing neurological degeneration such as can be induced by a stroke and the associated functional impairment which can result. Treatment using a compound of the invention can be remedial or therapeutic as by administering a compound following an ischemic event to mitigate the effects of that event. Treatment can also be prophylactic or prospective by administering a compound in anticipation that an ischemic event may occur, for example in a patient who is prone to stroke.

It is known that ischemic events can trigger a dramatic increase in extracellular concentrations of the excitatory amino acids glutamate and aspartate which can, in turn, cause prolonged neuronal excitation leading to a massive influx of calcium from extracellular to intracellular sites in brain neural cells. A calcium overload can thereby be created which leads to a cascade of events leading to cell catabolism and eventually resulting in cell death. The N-methyl-D-aspartate (NMDA) receptor complex is believed to play a significant role in the cascade of events leading to cell necrosis following an ischemic event.

The compounds provided by this invention may be useful in a variety of neurodegenerative disorders because they function as excitatory amino acid antagonists. They may do so indirectly, via allosteric modulation of the glutamate binding site, specifically by acting as antagonists of the strychnine-insensitive glycine receptor on the NMDA receptor complex. They may also do so directly, by binding to the glutamate site itself on the NMDA receptor complex.

3-Amino-4-methyl-2,5-dioxo-2,5-dihydro-1H-benz[b] azepine is disclosed in J. Org. Chem., 40, (1975), 3874–3877. Kokoku Patent No. Sho. 49-28754, published 29 Jul. 1974, refers to certain benz[b]azepines which bear an amino group or a dialkyl-substituted aminoalkylamino group, or a 3-substituent referred to as a "cyclic amino group composed of a 5- or 6-membered ring". Benz[b]azepines which bear a hydroxy or alkoxy group at the 3-position and which are unsubstituted at the the 4-position are referred to in published PCT patent application no. WO 92/11854; UK 1,340,334; Can. J. Chem., 52(4), 610–615; Mol. Pharmacol., 41(6), 1130–41; and J. Het. Chem., 26, (1989), 793.

According to the invention there is provided a method for the treatment of neurological disorders, comprising administering to a mammal in need of such treatment an effective amount of a compound of formula I or a compound of formula II (formulae set out, together with other formulae referred to by Roman Numerals, on pages following the Examples), wherein $R^1$, $R^2$, $R^3$ and $R^4$ are independently selected from hydrogen, (1–3C)perfluoroalkyl, halo, nitro and cyano;

$R^5$ is selected from hydrogen and (1–6C)alkyl;

$R^6$ and $R^7$ are independently selected from hydrogen, (1–6C)alkyl, (2–6C)alkenyl, (3–7C)cycloalkyl, (3–7C) cycloalkyl(1–6C)alkyl, aryl, aryl(1–6C)alkyl, heteroaryl, heteroaryl(1–6C)alkyl and $CH_2Y$ wherein Y is selected from $(CHOH)_nCH_2OH$ and $(CH_2)_mR^c$ wherein m is 0 to 5, n is 1 to 5 and $R^c$ is selected from hydroxy, (1–6C)alkoxy, (1–6C)alkoxycarbonyl, carboxy, and $NR^dR^e$ in which $R^d$ and $R^e$ are independently selected from hydrogen and (1–4C)alkyl or $R^d$ and $R^e$, together with the nitrogen atom to which they are attached, form a saturated 5-, 6- or 7-membered heterocyclic ring which optionally contains one additional heteroatom selected from nitrogen, oxygen and sulfur; or $R^6$ and $R^7$ together with the nitrogen atom to which they are attached, form a 5-, 6- or 7-membered heterocyclic ring which is bonded to said compound through said nitrogen atom, said heterocyclic ring optionally containing one additional heteroatom selected from nitrogen, oxygen and sulfur, and wherein said heterocyclic ring may be substituted with 0–2 substituents selected from (1–6C)alkyl, phenyl, phenyl (1–4C)alkyl, phenoxy and phenyl(1–4C)alkoxy;

$R^8$ is selected from hydrogen, halo, (1–6C)alkyl which may optionally bear a substituent selected from amino, (1–6C)acylamino, carboxy and carboxamido, aryl (1–6C)alkyl and heteroaryl(1–6C)alkyl;

and wherein each aryl moiety is selected from phenyl and naphthyl; each heteroaryl moiety is selected from 5- and 6-membered aromatic rings containing up to 3 heteroatoms independently selected from oxygen, sulfur, and nitrogen; and wherein each aryl or heteroaryl moiety may be substituted with 0–2 substituents selected from halo, cyano, hydroxy, carboxy, nitro, (1–6C)alkyl, (1–6C)alkoxy, (2–6C)alkenyl, phenyl, phenyl(1–4C)alkyl, phenoxy, phenyl(1–4C)alkoxy and (1–6C)alkoxycarbonyl;

or a pharmaceutically acceptable salt thereof; provided that in compounds of formula II, $R^8$ is not hydrogen; and excluding the compound of formula II in which $R^1$–$R^4$ are each hydrogen, $R^8$ is bromo and $R^5$ is hydrogen and its pharmaceutically acceptable salt.

Thus the present invention also provides a compound of formula I or formula II (as defined above), or a pharmaceutically acceptable salt thereof, for use in medicine; and in particular the use of a compound of formula I or of formula II (as defined above) for the manufacture of a medicament for treating neurological disorders.

The invention further provides pharmaceutical compositions for the treatment of neurological disorders comprising a compound of formula I or of formula II as defined above, or a pharmaceutically acceptable salt thereof, and a pharmaceutically acceptable diluent or carrier.

While not wishing to be bound by theory, it is believed that the compounds of this invention may be active as drugs in their own right and/or that they may be converted to the 3-hydroxy derivative in vivo, the 3-hydroxy derivative being active per se, and thus acting as prodrugs.

Many of the compounds of the present invention are novel and are hence provided as a further feature of the present invention. Thus, according to the present invention there is also provided a compound of formula I or formula II, and pharmaceutically acceptable salts thereof, wherein.

$R^1$, $R^2$, $R^3$ and $R^4$ are independently selected from hydrogen, (1-3C)perfluoroalkyl, halo, nitro and cyano;

$R^5$ is selected from hydrogen and (1-6C)alkyl;

$R^6$ and $R^7$ are independently selected from hydrogen, (1-6C)alkyl, (2-6C)alkenyl, (3-7C)cycloalkyl, (3-7C)cycloalkyl(1-6C)alkyl, aryl, aryl(1-6C)alkyl, heteroaryl, and heteroaryl(1-6C)alkyl and $CH_2Y$ wherein Y is selected from $(CHOH)_nCH_2OH$ and $(CH_2)_mR^c$ wherein m is 0 to 5, n is 1 to 5 and $R^c$ is selected from hydroxy, (1-6C)alkyl, (1-6C)alkoxy, (1-6C)alkoxycarbonyl, carboxy, and $NR^dR^e$ in which $R^d$ and $R^e$ are independently selected from hydrogen and (1-4C)alkyl or $R^d$ and $R^e$, together with the nitrogen atom to which they are attached, form a saturated 5-, 6- or 7-membered heterocyclic ring which optionally contains one additional heteroatom selected from nitrogen, oxygen and sulfur; or $R^6$ and $R^7$, together with the nitrogen atom to which they are attached, form a 5-, 6- or 7-membered heterocyclic ring which is bonded to said compound through said nitrogen atom, said heterocyclic ring optionally containing one additional heteroatom selected from nitrogen, oxygen and sulfur, and wherein said heterocyclic ring may be substituted with 0-2 substituents selected from (1-6C)alkyl, phenyl, phenyl(1-4C)alkyl, phenoxy, phenyl(1-4C)alkoxy;

$R^8$ is selected from hydrogen, halo, (1-6C)alkyl which may optionally bear a substituent selected from amino, (1-6C)acylamino, carboxy and carboxamido, aryl (1-6C)alkyl and heteroaryl(1-6C)alkyl;

and wherein each aryl moiety is selected from phenyl and naphthyl; each heteroaryl moiety is selected from 5- and 6-membered aromatic rings containing up to 3 heteroatoms independently selected from oxygen, sulfur, and nitrogen; and wherein each aryl or heteroaryl moiety may be substituted with 0-2 substituents selected from halo, cyano, hydroxy, carboxy, nitro, (1-6C)alkyl, (1-6C)alkoxy, (2-6C)alkenyl, phenyl, phenyl(1-4C)alkyl, phenoxy, phenyl(1-4C)alkoxy and (1-6C)alkoxycarbonyl;

provided that in compounds of formula II, $R^8$ is not hydrogen; and excluding the compound of formula II in which $R^1-R^4$ are each hydrogen, $R^8$ is bromo and $R^5$ is hydrogen; the compounds of formula I wherein $R^1-R^4$ and $R^6-R^7$ are each hydrogen and $R^8$ is hydrogen or methyl; the compounds of formula I in which $R^1-R^4$ and $R^8$ are each hydrogen and $R^6$ and $R^7$, together with the nitrogen atom to which they are attached, form a 5- or 6-membered ring; the compounds of formula I in which $R^1-R^4$ and $R^8$ are each hydrogen, $R^6$ is hydrogen and $R^7$ is $CH_2Y$ in which Y is $(CH_2)_mR^c$ and $R^c$ is $NR^dR^e$ in which $R^d$ and $R^e$ are (1-4C)alkyl; and their pharmaceutically acceptable salts.

In this specification the term "alkyl" includes both straight and branched chain radicals, but it is to be understood that references to individual radicals such as "propyl" embrace only the straight chain ("normal") radical, branched chain isomers such as "isopropyl" being referred to specifically.

"Halo" as used generally herein means fluoro, chloro, bromo, or iodo.

It will be appreciated by those skilled in the art that many of the compounds disclosed herein can exist and be drawn in various tautomeric forms, and all references to any particular structure are understood to include the various tautomeric forms thereof.

Particular values of (1-6C)alkyl include, for example, methyl, ethyl, propyl, isopropyl, butyl, isobutyl, pentyl, isopentyl, neopentyl, hexyl, and isohexyl.

Particular values of $R^1-R^4$ as (1-3C)perfluoroalkyl include, for example, trifluoromethyl, pentafluoroethyl, and heptafluoropropyl.

Particular values of $R^1-R^4$ as halo include, for example, fluoro, chloro, bromo, and iodo.

Particular values for an optional acylamino substituent include, for example, formyl, acetyl, propanoyl, isopropanoyl, butyryl, isobutyryl, pentanoyl and pivaloyl.

Particular values for $R^8$, $R^6$ or $R^7$ when arylalkyl include for example, benzyl, 1-phenylethyl and 2-phenylethyl.

Particular values for $R^8$, $R^6$ or $R^7$ when heteroarylalkyl include, for example, pyridylmethyl, pyrimidinylmethyl and imidazoylmethyl.

Particular values for $R^6$ and $R^7$ when alkenyl include, for example, vinyl, allyl, but-2-enyl, but-3-enyl and 2-methyl-2-propenyl.

Particular values for $R^6$ and $R^7$ when cycloalkyl include, for example, cyclopropyl, cyclobutyl, cyclopentyl and cyclohexyl.

Particular values for $R^6$ and $R^7$ when cycloalkylalkyl include, for example, cyclopropylmethyl, cyclobutylmethyl, cyclopentylmethyl, 2-(cyclopropyl)ethyl and cyclohexylmethyl.

Particular values for $R^c$ when alkoxy include, for example, methoxy, ethoxy, propoxy, isopropoxy, butoxy, isobutoxy and tertbutoxy.

Particular values for $R^c$ when alkoxycarbonyl include, for example, methoxycarbonyl, ethoxycarbonyl, propoxycarbonyl, isopropoxycarbonyl, butoxycarbonyl, isobutylcarbonyl and tertbutoxycarbonyl.

Particular values for $R^d$ and $R^e$ when alkyl include, for example, methyl, ethyl, propyl, isopropyl and butyl.

Particular values for —$NR^dR^e$, when $R^d$ and $R^e$ together with the nitrogen atom to which they are attached, form a saturated 5-, 6- or 7-membered ring include, for example, pyrrolidinyl, piperidinyl, 4-morpholinyl, piperazinyl and perhydroazepinyl.

Particular values of 5- to 7-membered rings, bonded through nitrogen and optionally containing one additional heteroatom selected from nitrogen, oxygen, and sulfur, which rings can be formed by $R^6$ and $R^7$ together with the nigrogen to which they are attached, include imidazolyl, pyrrolidinyl, pyrrolo, pyrazolyl, piperidinyl, 4-morpholinyl, piperazinyl, 1,4-thiazin-4-yl, 1,4-oxazin-4-yl, and perhydroazepinyl.

Particular values for optional substituents which may be present on a 5-, 6- or 7- membered heterocyclic ring include;

for alkyl; methyl, ethyl, propyl, isopropyl and butyl;

for phenylalkyl; benzyl, 1-phenylethyl and 2-phenylethyl;

for phenylalkoxy; phenylmethoxy, 1-phenylethoxy, 2-phenylethoxy and 3-phenylpropoxy.

Particular values for 5- or 6-membered heteroaryl moieties containing up to 3 heteroatoms independently selected from N, O, and S include pyridyl, pyrrolo, pyrazinyl, pyrimidinyl, pyridazinyl, isothiazolyl, imidazolyl, isoxazolyl, thiazolyl, oxazolyl and triazolyl.

Particular values for an optional substituent which may be present on an aryl or heteroaryl moiety include:

for alkyl; methyl, ethyl, propyl, isopropyl and butyl;

for alkoxy; methoxy ethoxy, propoxy, isopropoxy and butoxy;

for alkenyl; vinyl, allyl, but-2-enyl, but-3-enyl and 2-methyl-2-propenyl;

for phenylalkyl; benzyl, 1-phenylethyl and 2-phenylethyl;

for phenylalkoxy; benzyloxy 1-phenylethoxy and 2-phenylethoxy;

for alkoxycarbonyl; methoxycarbonyl, ethoxycarbonyl, propoxycarbonyl, isopropoxycarbonyl, butoxycarbonyl, isobutyoxycarbonyl and tert-butoxycarbonyl.

More particular values for aryl moieties (for an aryl or arylalkyl moiety in $R^6$, $R^7$ or $R^8$) with 0–2 substituents include phenyl, 2-, 3-, and 4-halophenyl, 2-, 3- and 4-hydroxyphenyl, 2-, 3- and 4-cyanophenyl, 2-, 3-, and 4-nitrophenyl, 2-, 3-, and 4-methylphenyl, 2-, 3-, and 4-ethylphenyl, 2-, 3-, and 3-propylphenyl, 2-, 3- and 4-methoxyphenyl, 2-, 3- and 4-ethoxyphenyl, 2-, 3- and 4-propoxyphenyl, 2,4-dihalophenyl, 2,3-dihalophenyl, 3,4-dibenzyloxyphenyl, 4-methoxycarbonylphenyl and naphthyl.

More particular values of (1–6C)alkyl include methyl, ethyl, and propyl.

More particular values of $R^1$–$R^4$ as (1–3C)perfluoroalkyl include trifluoromethyl and pentafluoroethyl.

More particular values of $R^1$—$R^4$ as halo include fluoro, chloro, and bromo.

In a particular embodiment, $R^8$ is selected from hydrogen, (1–6C)alkyl which may optionally bear a substituent selected from amino, (1–6C)acylamino, carboxy, and carboxamido; aryl(1–6C)alkyl and heteroaryl(1–6C)alkyl.

Values of $R^6$ and $R^7$ of particular interest include, for example, hydrogen, (1–6C)alkyl, (3–7C)cycloalkyl(1–6C) alkyl, aryl, aryl(1–6C)alkyl, and heteroaryl(1–6C)alkyl) and $CH_2Y$ wherein Y is selected from $(CHOH)_nCH_2OH$ and $(CH_2)_mR^c$ wherein m is 0 to 5, n is 1 to 5 and $R^c$ is selected from hydroxy, (1–6C)alkoxycarbonyl and $NR^dR^e$ in which $R^d$ and $R^e$ are independently selected from (1–4C)alkyl, or $R^6$ and $R^7$, together with the nitrogen atom to which they are attached, form a 5-, 6- or 7-membered heterocyclic ring which is bound to said compound through said nitrogen atom, said heterocyclic ring optionally containing one additional heteroatom selected from nitrogen, oxygen and sulphur and wherein said heterocyclic ring may be substituted with 0–2 substituents selected from (1–6C)alkyl, phenyl, phenyl(1–4C)alkyl, phenoxy and phenyl(1–4C)alkoxy; and wherein an aryl or heteroaryl moiety may be substituted with 0–2 substitutes selected from halo, cyano, hydroxy, carboxy, nitro, (1–6C)alkyl, (1–6C)alkoxy, (2–6C)alkenyl, phenyl, phenyl(1–4C)alkyl, phenoxy, phenyl(1–4C)alkoxy and (1–6C)alkoxycarbonyl.

Values of $R^8$ of particular interest include, for example, hydrogen, (1–6C)alkyl, halo and phenyl(1–6C)alkyl, especially hydrogen, (1–6C)alkyl and iodo.

A value of $R^1$, $R^2$, $R^3$ and $R^4$ of particular interest include, for example, hydrogen and halo (such as chloro or bromo).

It is generally preferred, for example, that the aryl moiety is a phenyl moiety (optionally substituted as herein defined).

It is generally preferred, for example, that when —$NR^6R^7$ represents a heterocyclic ring, said ring is selected from morpholino, imidazolyl, pyrrolidinyl, pyrrolo, pyrazolyl, piperidinyl [which may optionally bear a 4-substituent selected from (1–6C)alkyl, phenyl(1–6C)alkyl, phenoxy and phenyl], 4-morpholinyl, piperazinyl [which may optionally bear a 4-substituent selected from (1–6C)alkyl, phenyl (1–6C)alkyl and phenyl] and perhydroazepinyl.

It is generally preferred, for example, that when $R^8$ is halo, it is iodo.

It is generally preferred, for example, that $R^5$ is hydrogen.

It is generally preferred, for example, that $R^8$ is hydrogen, methyl or iodo.

It is generally preferred, for example, that $R^1$, $R^2$ and $R^4$ are each hydrogen and $R^3$ is halo (such as chloro).

It is generally preferred, for example, that $R^6$ is selected from hydrogen, (1–6C)alkyl, aryl, aryl(1–6C)alkyl and $CH_2Y$ wherein Y is selected from $(CHOH)_nCH_2OH$ and $(CH_2)_mR^c$ wherein m is 0 to 5, n is 1 to 5 and $R^c$ is (1–6C)alkoxycarbonyl; and $R^7$, is hydrogen or (1–6C)alkyl; or $R^6$ and $R^7$ together with the nitrogen atom to which they are attached from a 5-, 6- or 7-membered heterocyclic ring which is bound to said compound through nitrogen atom, said heterocyclic ring optionally containing one additional heteroatom selected from nitrogen, oxygen and sulphur and wherein said heterocyclic ring may be substituted with 0–2 substituents selected from (1–6C)alkyl, phenyl, phenyl (1–4C)alkyl, phenoxy and phenyl(1–4C)alkoxy; and wherein an aryl moiety represents a phenyl moiety and wherein an aryl or heteroaryl moiety may be substituted with 0–2 substituents selected from halo, hydroxy, carboxy, nitro, (1–6C)alkyl, (1–6C)alkoxy, (2–6C)alkenyl, phenyl, phenyl (1–4C)alkyl, phenoxy, phenyl(104C)alkoxy and (1–6C) alkoxycarbonyl.

Specific values for $R^1$, $R^2$ and $R^4$ include for example hydrogen; and for $R^3$ include hydrogen and chloro.

Specific values for $R^8$ include, for example, hydrogen, benzyl, methyl, 4-methoxycarbonylbenzyl and iodo.

Specific values for $R^5$ include, for example, hydrogen and methyl.

Specific values for —$NR^6R^7$ include, for example, amino, methylamino, dimethylamino, diethylamino, phenethylamino, 4-morpholino, allylamino, α-methylbenzylamino, t-butoxycarbonylmethylamino, 1-perhydroazepinyl, 1-pyrrolidinyl, anilino, pyrrolo, 4-phenylpiperazin-1-yl, 4-benzylpiperazin-1-yl, piperidino, 2-(N,N-diethylamino)ethylamino, glucamino, 4-phenoxypiperadino, benzylamino, cyclopropylmethylamino, 3,4-dibenzyloxyphenethylamino, 2-(4-imidazolyl)ethylamino, N,N-bis(2-hydroxyethyl) amino, and N-(2-hydroxyethyl)amino.

As indicated above, the present invention relates to compounds of formula I and to compounds of formula II. Thus, one aspect of the present invention relates to compounds of formula I and thus provides a method of treating neurological disorders comprising administering an effective amount of a compound of formula I to a mammal in need of such treatment, pharmaceutical compositions containing compounds of formula I, novel chemical compounds of compounds is of formula I, and processes for their preparation. A further aspect relates to compounds of formula II and thus provides a method of treating neurological disorders comprising administering an effective amount of a compound of formula II to a mammal in need of such treatment, pharmaceutical compositions containing compounds of formula II, novel chemical compounds of compounds of formula II, and processes for their preparation.

In a particular embodiment of the present invention there is provided a method of treating neurological disorders, comprising administering to a mammal in need of such treatment an effective amount of a compound of formula I wherein $R^1$, $R^2$, $R^3$ and $R^4$ are independently selected from:
hydrogen,
(1–3C)perfluoroalkyl,
halo, nitro and cyano;

$R^6$ and $R^7$ are independently selected from hydrogen,
$CH_2Y$ wherein Y is selected from $(CH_2)_mOH$ and $(CHOH)_nCH_2OH$ wherein m is 0 to 5 and n is 1 to 5, aryl, and aryl(1–6C)alkyl wherein each aryl moiety is selected from phenyl and naphthyl each of which may be substituted with 0–2 substituents selected from halo, cyano hydroxyl, nitro, (1–6C)alkyl, (1–6C)alkoxy, vinyl, and allyl; and heteroaryl, and heteroaryl(1–6C)alkyl wherein each heteroaryl moiety is selected from 5- and 6-membered aromatic rings containing up to 3 heteroatoms independently selected from oxygen, sulfur, and nitrogen;

or $R^6$ and $R^7$, together with the nitrogen atom to which they are attached, form a 5-, 6- or 7-membered heterocyclic ring which is bonded to said compound through said nitrogen atom, said heterocyclic ring optionally containing one additional heteroatom selected from nitrogen, oxygen and sulfur;

$R^8$ is selected from hydrogen,
(1–6C)alkyl which may optionally bear a substituent selected from amino, (1–6C)acylamino, carboxy, and carboxamido; and aryl(1–6C)alkyl;

or a pharmaceutically acceptable salt thereof.

Particular, preferred and specific values are the appropriate values mentioned above. In a further embodiment there is provided the corresponding 3-hydroxy compounds to the compounds of formula I defined in the preceeding paragraph.

A particular group of compounds of interest include those of formula I wherein $R^1$, $R^2$, $R^3$ and $R^4$ are independently selected from: hydrogen, (1–3C)perfluoroalkyl, halo, nitro and cyano;

$R^6$ and $R^7$ are independently selected from hydrogen,
CH$_2$Y wherein Y is selected from (CH$_2$)$_m$OH and (CHOH)$_n$CH$_2$OH wherein m is 0 to 5 and n is 1 to 5, aryl, and aryl(1–6C)alkyl wherein each aryl moiety is selected from phenyl and naphthyl each of which may be substituted with 0–2 substituents selected from halo, cyano hydroxyl, nitro, (1–6C)alkyl, (1–6C)alkoxy, vinyl, and allyl; and heteroaryl, and heteroaryl(1–6C)alkyl wherein each heteroaryl moiety is selected from 5- and 6-membered aromatic rings containing up to 3 heteroatoms independently selected from oxygen, sulfur, and nitrogen;

$R^8$ is selected from
hydrogen,
(1–6C)alkyl which may optionally bear a substituent selected from amino, (1–6C)acylamino, carboxy, and carboxamido; and
aryl(1–6C)alkyl;

but excluding the compounds wherein $R^1$–$R^4$ and $R^6$–$R^7$ are each hydrogen and $R^8$ is hydrogen or methyl;
and pharmaceutically acceptable salts thereof.

Particular, preferred and specific values are the appropriate values mentioned above. In a further embodiment there is provided the corresponding 3-hydroxy compound to the compounds of formula I defined in the preceeding paragraph.

In a particular group of novel compounds of formula I, $R^1$, $R^2$, $R^3$ and $R^4$ are independently selected from hydrogen, (1–3C)perfluoroalkyl, halo, nitro and cyano;

$R^6$ and $R^7$ are independently selected from hydrogen, (1–6C)alkyl, (2–6C)alkenyl, (3–7C)cycloalkyl, (3–7C)cycloalkyl(1–6C)alkyl, aryl, aryl(1–6C)alkyl, heteroaryl, and heteroaryl(1–6C)alkyl and CH$_2$Y wherein Y is selected from (CHOH)$_n$CH$_2$OH and (CH$_2$)$_m$R$^c$ wherein m is 0 to 5, n is 1 to 5 and R$^c$ is selected from hydroxy, (1–6C)alkoxy, (1–6C)alkoxycarbonyl, carboxy, and NR$^d$R$^e$ in which R$^d$ and R$^e$ are hydrogen or R$^d$ and R$^e$, together with the nitrogen atom to which they are attached, form a saturated 5-, 6- or 7-membered heterocyclic ring which optionally contains one additional heteroatom selected from nitrogen, oxygen and sulfur; or $R^8$ is selected from hydrogen, halo, (1–6C)alkyl which may optionally bear a substituent selected from amino, (1–6C)acylamino, carboxy and carboxamido, aryl (1–6C)alkyl and heteroaryl(1–6C)alkyl;

and wherein each aryl moiety is selected from phenyl and naphthyl; each heteroaryl moiety is selected from 5- and 6-membered aromatic rings containing up to 3 heteroatoms independently selected from oxygen, sulfur, and nitrogen; and wherein each aryl or heteroaryl moiety may be substituted with 0–2 substituents selected from halo, cyano, hydroxy, carboxy, nitro, (1–6C)alkyl, (1–6C)alkoxy, (2–6C)alkenyl, phenyl, phenyl(1–4C)alkyl, phenoxy, phenyl(1–4C)alkoxy and (1–6C)alkoxycarbonyl;

but excluding the compounds wherein $R^1$–$R^4$ and $R^6$–$R^7$ are each hydrogen and $R^8$ is hydrogen or methyl; and pharmaceutically acceptable salts thereof.

Particular, preferred and specific values are the appropriate values mentioned above.

A further group of compounds of interest include those of formula II wherein $R^1$, $R^2$, $R^3$ and $R^4$ are independently selected from:
hydrogen,
(1–3C)perfluoroalkyl,
halo, nitro and cyano;

$R^5$ is hydrogen or (1–6C)alkyl;

$R^8$ is selected from
(1–6C)alkyl which may optionally bear a substituent selected from amino, (1–6C)acylamino, carboxy, and carboxamido; and
aryl(1–6C)alkyl;

and pharmaceutically acceptable salts thereof.

Particular, preferred and specific values are the appropriate values mentioned above.

Compounds of the invention which are of particular interest include the compounds described in the accompanying Examples, and their pharmaceutically acceptable salts, and are hence provided as a further feature of the present invention. In particular, the present invention provides a compound selected from those described in Examples 1, 2, 5, 19, 15, 34, 18, 20, 35 and 37, and their pharmaceutically acceptable salts thereof.

The Benz[b]azepines of the present invention can be made by processes which include processes known in the chemical arts for the production of structurally analogous compounds. Such processes for the manufacture of novel benz[b]azepines as defined above are provided as further features of the invention and are illustrated by the following procedures in which the meanings of generic radicals are as given above unless otherwise qualified. Thus, according to the present invention there is also provided a process for the preparation of novel benz[b]azepines of formula I and II, which processes are selected from:

(a) For compounds of formula I, reacting a compound of formula II wherein $R^5$ is an alkyl group with an amine of formula R$^6$R$^7$NH.

Suitable values of alkyl groups include, for example, (1–6C)alkyl such as methyl or ethyl. The reaction is generally carried out at a temperature from about 0° C. to about 150° C., and the reaction can be conducted using the amine neat as reactant and solvent, or if desired the reaction can be conducted using a solvent such as an alcohol of formula $R^5OH$ (eg. methanol) or a solvent such as dimethylformamide. As a particular example of suitable reaction conditions the compound of formula II may be heated with the amine of formula $R^6R^7NH$ at a temperature of about 80° C. using the amine of formula $R^6R^7NH$ as solvent or at a temperature of about 80° C. in a solvent of dimethylformamide, or at reflux in a solvent of methanol.

(b) For compounds of formula I in which $R^8$ is hydrogen, reacting a compound of formula II in which $R^8$ is halo with an amine of formula $R^6R^7NH$.

Suitable values for $R^8$ in the compound of formula II used as starting material include, for example, iodo and bromo, with iodo being the preferred value. The reaction is generally carried out in neat amine at a temperature between ambient temperature and the reflux temperature of the reaction mixture. In some instances it may be desirable to carry the reaction out in a pressure vessel with heating, for example to a temperature such as 60° C.

This reaction may also be employed to prepare compounds of formula I in which $R^8$ is halo, but the major product in most instances is, as indicated above, the compound of formula I in which $R^8$ is hydrogen.

(c) For compounds of formula I or II in which $R^8$ is halo, halogenating a compound of formula I or II (as appropriate) in which $R^8$ is hydrogen.

Suitable reaction conditions include, for example, the use of halogens such as bromine or chlorine and halogenating agents such as iodine monochloride and xenon tetrafluoride or hexafluoride. The reaction is generally carried out in a suitable solvent such as glacial acetic acid and at a temperature from about 0° C. to the reflux temperature of the reaction mixture.

(d) For compounds of formula II in which $R^5$ is hydrogen, treating a compound of formula II in which $R^5$ is alkyl with a boron trihalide.

Suitable values for $R^5$ include, for example, (1–6C)alkyl such as methyl or ethyl. A particularly suitable boron trihalide is, boron tribromide. The reaction is generally carried out in an inert solvent such as dichloromethane at ambient temperature.

(e) For compounds of formula I or II in which $R^8$ is other than hydrogen, reacting a compound of formula I or II (as appropriate) in which $R^8$ is halo with a compound of formula $R^{8'}SnL_3$, in which L is a suitable ligand and $R^{8'}$ may take any of the values herein defined for $R^8$ except hydrogen and halo, in the presence of a suitable catalyst.

Suitable values for L include, for example, (1–6C)alkyl, with butyl being preferred. Suitable catalysts include, for example, palladium (II) catalysts such as trans dibenzyl palladium chloride catalysts. A particularly suitable catalyst is trans-benzyl(chloro)-bis(triphenylphosphine)palladium (II). The reaction is generally carried out in an inert hydrocarbon solvent such as toluene at a temperature from about ambient temperature to the reflux temperature of the reaction mixture, preferably at the reflux temperature of the reaction mixture.

This process is generally preferred to that described in (g) below when one or more of $R^1-R^4$ is other than hydrogen.

(f) For those compounds of formula I in which —$NR^6R^7$ represents a pyrrolo group, reacting a compound of formula I in which $R^6$ and $R^7$ are both hydrogen with a 2,5-dialkoxytetrahydrofuran.

Suitable dialkoxytetrahydrofurans include, for example, 2,5-dimethoxytetrahydrofurans. The reaction is generally carried out in a solvent such as glacial acetic acid and at a temperature from about ambient temperature to the reflux temperature of the reaction mixture, and preferably at the reflux temperature of the reaction mixture.

(g) For compounds of formula II in which $R^8$ is other than hydrogen, reacting a compound of formula II in which $R^8$ is hydrogen with a compound of formula $R^8Z$, in which Z is a suitable leaving group, in the presence of a base.

Suitable values for Z include, for example, halo such as bromo or iodo, mesyl and tosyl. Suitable bases include, for example, alkyllithium compounds such as butyl lithium. The reaction will, in general, carried out in the presence of two equivalents of the base (or a slight excess over two equivalents) and in the presence of an amine such as diisopropylamine. An alkali metal salt such as lithium chloride may also be present, and the reaction may conveniently be carried out at a temperature of about −78° to about −20° C., thereby forming a dianion, followed by reacting the dianion thereby prepared with a corresponding compound of formula $R^8Z$ (eg $R^8I$) at a temperature of about −40° C. to about 25° C. Alternatively, the dianion may be prepared by treatment of a compound of formula II in which $R^8$ is halo, for example bromo or iodo, with an organometallic reagent such as, for example, butyl lithium, in an inert solvent such as tetrahydrofuran, conveniently at a temperature of about −78° C., and reacted with the required compound of formula $R^8Z$ as described alone.

A compound of formula II wherein $R^8$ is H can be made by reacting a corresponding alkyl enol ether of formula III with sodium azide in neat trifluoromethanesulfonic acid or concentrated sulfuric acid (Schmidt reaction) at a temperature of about 0° C. to about room temperature. Trifluoromethanesulfonic acid is preferred in cases where any one or more of $R^1-R^4$ is halogen. $R^5$ is preferably methyl or ethyl to facilitate the Schmidt reaction.

A methyl enol ether of formula III can be made by reacting a corresponding hydroxy naphthoquinone of formula IV with a corresponding alcohol having the formula $R^5OH$, such as methanol or ethanol, in the presence of a suitable acid such as anhydrous hydrogen chloride. Hydroxy naphthoquinones of formula IV can be made by oxidizing a corresponding tetralone of formula V or of formula Va. The oxidation can be effected conveniently as a one-pot process in a suitable solvent such as tert-butanol and in the presence of a suitable base such as potassium tert-butoxide, with oxygen bubbled through the reaction mixture. In a preferred process the hydroxy naphthoquinone of formula IV may be oxidised to the corresponding tetralone of formula V by bubbling oxygen through a solution of potassium bis (trimethylsilyl)amide in dimethylformamide, adding the hydroxy naphthoquinone and continuing to bubble oxygen through the reaction mixture until the oxidation is complete. This process is described in the alternative procedure described in the second part of Example 1(c). It will also be appreciated by those skilled in the art that suitable stepwise or multi-pot variations of the one-pot process can be implemented.

Many tetralones of formula V and/or Va suitable for use in the invention are either available commercially or can be made by procedures already known in the art. For example, a 1-tetralone of formula V can be made by cyclizing a corresponding acid of formula VI under acidic conditions, for example with polyphosphoric acid with the application of heat. A 2-tetralone of formula Va can be made by ethylene insertion into the corresponding phenylacetic acid chloride of formula VIa, followed by cyclization, following the general method of Rosowsky et al, J. Org. Chem., 33, 4288 (1968).

Compounds of formula VI can be made by reducing a corresponding ketone, for example, by reducing a compound of formula VII by methods known to the art, e.g. a Wolff-Kishner reduction for the reduction of carbonyl groups using hydrazine and base.

Compounds of formula VIa can be made by converting a benzylic alcohol of formula VIII (X=OH) to a corresponding benzylic chloride (X=Cl) (e.g., by reacting with an appropriate reactant such as thionyl chloride), followed by reacting the benzyl chloride thus formed with a suitable alkali metal cyanide (e.g., sodium cyanide) to effect cyanide displacement of chloride and thereby form a corresponding benzylic cyanide (X=CN). An acid of formula VIa can be prepared as known in the art by hydrolyzing the benzylic cyanide under acidic conditions.

Alternatively, acids of formula VIa can be formed by brominating a toluene corresponding to formula VIII wherein X=H to form the corresponding benzylic bromide (X=Br), followed by displacement with cyanide as described above to form acid VIa.

It is noted that many enol ethers of formula III can also be made along the lines generally disclosed in S. T. Petri at. al., Org. Syn., 69, 220 and in J. M. Heerding and H. W. Moore, J. Org. Chem., 56, 4048–4050, (1991). The synthesis is generally illustrated in Scheme I (set forth on pages following the Examples) as follows. Organolithium compound 10 can be reacted with semisquarate or semisquaric acid compound 12 to thereby produce 4-(disubstitutedaryl)-3-alkoxy-4-hydroxy-2-cyclobutenone 14. It is noted that semisquarate compound 12 can be readily obtained, as set forth in Heerding and Moore, supra, by treatment of a dialkyl squarate (such as diethyl, diisopropyl, or dibutyl squarate, all available commercially from Aldrich) with a suitable reducing agent such as lithium tri-tert-butoxyaluminohydride, followed by hydrolysis of the intermediate 13 thereby obtained in aqueous hydrochloric acid. Compound 14 can in turn be converted, by heating in a suitable solvent such as xylene, to the hydroquinone 16. Hydroquinone 16 can then be oxidized (e.g. with ferric chloride) to the corresponding naphthoquinone 18. If necessary preparatory to conducting the Schmidt reaction on the naphthoquinone, naphthoquinone 18 can be transetherified, for example with methanolic hydrochloric acid, thereby yielding the methoxy naphthoquinone 20 having formula III.

If not commercially available, the necessary starting materials for the procedures such as that described above may be made by procedures which are selected from standard organic chemical techniques, techniques which are analogous to the synthesis of known, structurally similar compounds, or techniques which are analogous to the above described procedure or the procedures described in the examples.

It will also be appreciated that certain of the various optional substituents in the compounds of the invention may be introduced by standard aromatic substitution reactions or generated by conventional functional group modifications either prior to or immediately following the processes above, and as such are included in the process aspect of the invention. Such reactions and modifications include, for example, introduction of nitro or halogeno. The reagents and reaction conditions for such procedures are well known in the chemical art.

Pharmaceutically acceptable salts may be formed with some compounds of the present invention using standard procedures well known in the art, for example by reacting a sufficiently basic compound of formula I or II with a suitable acid affording a physiologically acceptable anion, or by reacting a sufficiently acidic compound of formula I or II with a suitable base affording a physiologically acceptable cation.

When used to intervene therapeutically following a stroke, a benz[b]azepine of the present invention is generally administered as an appropriate pharmaceutical composition which comprises a benz[b]azepine of the present invention (as defined hereinbefore) together with a pharmaceutically acceptable diluent or carrier, the composition being adapted for the particular route of administration chosen. Such compositions are provided as a further feature of the invention. They may be obtained employing conventional procedures and excipients and binders and may be in a variety of dosage forms. For example, they may be in the form of tablets, capsules, solutions or suspensions for oral administration; in the form of suppositories for rectal administration; and in the form of sterile solutions or suspensions for administration by intravenous or intramuscular injection or infusion.

The dose of compound of the present invention which is administered will necessarily be varied according to principles well known in the art taking account of the route of administration, the severity of the ischemic disorder, and the size and age of the patient. In general, a compound of formula I or of formula II will be administered to a warm blooded animal (such as man) so that an effective dose is received, for example an intravenous dose in the range of about 0.1 to about 10 mg/kg body weight.

It will be apparent to those skilled in the art that a compound of the present invention can be co-administered with other therapeutic or prophylactic agents and/or medicaments that are not medically incompatible therewith.

As mentioned previously, the compounds of the present invention (and their pharmaceutically acceptable salts) are useful in treating neurological disorders in mammals such as man.

The actions of compounds of formula I as antagonists at the glycine receptor of the NMDA receptor complex can be shown by standard tests such as the $[^3H]$-glycine binding assay, by functional assays in vitro such as tests for measuring glutamate evoked contractions of the guinea pig ileum, and by tests in vivo such as ischemia induced by carotid occlusion in the gerbil model. The beneficial pharmacological properties of the compounds of the present invention may be demonstrated using one or more of these techniques.

In the $[^3H]$-glycine binding assay, neuronal synaptic membranes are prepared from adult (about 250 g) male Sprague-Dawley rats. Freshly dissected cortices and hippocampi are homogenized in 0.32M sucrose (110 mg/mL). Synaptosomes are isolated by centrifugation (1000×g, 10 min), the supernatant is pelleted (20,000×g, 20 min) and resuspended in double-distilled water. The suspension was centrifuged for 20 minutes at 8,000×g. The resulting supernatant and buffy coat are washed twice (48,000×g, 10 mins, resuspension in double-deionized water). The final pellet is quickly frozen (dry ice\ethanol bath) under double-deionized water and stored at −70° C.

On the day of the experiment, thawed synaptic membranes are homogenized with a Brinkmann Polytron (tm, Brinkmann Instruments, Westbury, N.Y.) tissue homogenizer in 50 mM tris(hydroxymethyl)-aminomethane citrate, pH 7.1. The membranes are incubated with 0.04% Sufact-AMPS X100 (tm, Pierce, Rockford, Ill.) in buffer for 20 minutes at 37° C. and washed six times by centrifugation (48,000×g, 10 min) and resuspended in buffer. The final pellet is homogenized at 200 mg wet weight/mL of the buffer for the binding assay.

For [$^3$H]-glycine binding at the N-methyl-D-aspartate receptor, 20 nM [$^3$H]-glycine (40–60 Ci/mmol, New England Nuclear, Boston, Mass.) is incubated with the membranes suspended in 50 mM tris (hydroxymethyl) aminomethane citrate, pH 7.1 for 30 minutes at 4° C. Glycine, 1 mM, is used to define the nonspecific binding. Bound [$^3$H]-glycine is isolated from free using a Brandel (Biomedical Research and Development Laboratories, Gaithersburg, Md.) cell harvester for vacuum filtration over glass fiber filters (Whatman GF/B from Brandel, Gaithersburg, Md.) presoaked in 0.025% polyethylenimine. The samples retained on the glass fiber filters are rinsed 3 times with a total of 2.5 mL ice cold buffer. Radioactivity is estimated by liquid scintillation counting. $IC_{50}$ values are obtained from a least-squares regression of a logit-log transformation of the data.

By way of illustration, the compound of formula I described in Example 12 gave an $IC_{50}$ of about $4.7 \times 10^{-5}$M; and the compound of formula I described in Example 19 gave an $IC_{50}$ of about $4.3 \times 10^{-5}$M.

For glutamate evoked contractions of the guinea pig ileum, the methodology is as described previously (Luzzi et. al., Br. J. Pharmacol., 95, 1271–1277 (1989). The longitudinal muscle and associated myenteric plexus are removed and placed in oxygenated modified Krebs-Henseleit solution (118 mM NaCl, 4.7 mM KCl, 2.5 mM $CaCl_2$, 1.2 mM $KH_2PO_4$, 25 mM $NaHCO_3$, and 11 mM glucose). Tissues are suspended on glass rods in organ baths under a resting tension of 0.5 g. After an initial depolarization with 80 mM potassium to remove possible blockade of the NMDA receptor channel complex with magnesium, twitch responses are evoked with 100 µM glutamate. Isometric mechanical responses are recorded. Tissues are equilibrated for at least 2 hours prior to addition of compounds.

A dose response curve for the effect of the unknown on the magnitude of the glutamate-evoked contractions is generated. Glutamate-evoked contractions are generated at 20 minute intervals, with the test compound added 5 minutes before the glutamate. The magnitude of the contraction with each dose of the unknown is expressed relative to the control, the third contraction evoked by 100 µM glutamate alone in the same tissue bath. The $IC_{50}$ is obtained from a least-squares regression of a logit-log transformation of the data.

After the last contraction for the dose-response curve, 100 µM glycine is added to the bath 10 minutes after the previous addition of glutamate. 10 minutes later the estimated $IC_{50}$ to $IC_{70}$ dose of the test compound is added and 10 minutes later glutamate is used to evoke the contraction. The "glycine reversal" is the ability of glycine to compete with the unknown and to prevent the inhibition previously seen by the dose of the unknown.

When testing in vivo using the gerbil ischemic model, adult female Mongolian gerbils (50–70 g) are anesthetized with 2 to 3% halothane. The bilateral common carotid arteries at the neck are exposed and occluded with microaneurysm clips. After 10 min (unless specified), the clips are removed and the blood flow through the carotid arteries is restored and the skin is sutured. Test compounds are administered intraperitoneally both pre- and post-occlusion, for example 45 minutes before and 5 minutes after occlusion of the carotid arteries. Sham-operated animals are treated in the same manner except that the arteries are not clamped. Gross behavioral observations along with motor activity are recorded for 2 hr on the first (24 hr) day following the occlusion. After 4 days, subjects are sacrificed (decapitation), brains are removed, fixed, sectioned and stained with hematoxylin/eosin and cresyl violet.

The brain sections are rated for neuronal damage in the hippocampus using the following rating scale:

0=undamaged, normal

1=slight damage (up to 25%)—restricted CA1/subiculum border

2=moderate damage (up to 50%)—obvious damage, restricted to less than half of CA1 field 3=marked damage (up to 75%)—involving greater than half of CA1 field 4=damage extending beyond CA1 field Results can be reported as the percentage of neuroprotection afforded by a particular dose and dosing regimen.

Sections (7 micron) are evaluated from each brain. Occasionally, asymmetrical damage may be noted and the rating assigned is the average score of the two sides. The average brain damage rating score for each group is recorded, and the damage scores of the drug treated group are compared to the vehicle-treated group using Wilcoxcon-Rank Sum test.

By way of illustration, the compound of formula I described in Example 12 below gave about 62% neuroprotection (relative to sham-operated control) when dosed twice with 20 mg/kg body weight intraperitioneally (ip) according to the above regimen; the compound of formula I described in Example 19 gave about 80% neuroprotection when dosed twice with 20 mg/kg body weight (ip); and the compound of formula I described in Example 6 gave about 43% neuroprotection when dosed twice with 20 mg/kg body weight (ip).

The invention will now be illustrated by the following non-limiting Examples in which, unless otherwise stated:

(i) temperatures are given in degrees Celsius (°C.) operations were carried out at room or ambient temperature, that at a temperature in the range of 18°–25° C.;

(ii) organic solutions were dried over anhydrous magnesium sulfate; evaporation of solvent was carried out using a rotary evaporator under reduced pressure (600–4000 pascals; 4.5–30 mm Hg) with a bath temperature of up to 60° C.;

(iii) chromatography means flash chromatography on silica gel; thin layer chromatography (TLC) was carried out on silica gel plates;

(iv) in general, the course of reactions was followed by TLC and reaction times are given for illustration only;

(v) melting points are uncorrected and (dec) indicates decomposition; the melting points given are those obtained for the materials prepared as described; polymorphism may result in isolation of materials with different melting points in some preparations;

(vi) final products had satisfactory proton nuclear magnetic resonance (NMR) spectra;

(vii) yields are given for illustration only and are not necessarily those which may be obtained by diligent process development; preparations were repeated if more material was required;

(viii) when given, NMR data is in the form of delta values for major diagnostic protons, given in parts per million (ppm) relative to tetramethylsilane (TMS) as an internal standard, determined at 300 MHz using perdeuterio dimethyl sulfoxide (DMSO-$d_6$) as solvent; conventional abbreviations for signal shape are used; coupling constants (j) are given in Hz;

(ix) chemical symbols have their usual meanings; SI units and symbols are used;

(x) reduced pressures are given as absolute pressures in pascals (Pa); elevated pressures are given as gauge pressures in bars;

(xi) solvent ratios are given in volume:volume (v/v) terms; and (xii) mass spectra (MS) were run with an electron energy of 70 electron volts in the chemical ionization (CI) mode using a direct exposure probe; where indicated ionization was effected by electron impact (EI) or fast atom bombardment (FAB); values for m/z are given; generally, only ions which indicate the parent mass are reported.

Example 1

3-Amino-8-chloro-2,5-dioxo-2,5-dihydro-1H-benz[b]azepine

8-Chloro-3-methoxy-2,5-dioxo-2,5-dihydro-1H-benz[b]azepine (0.4 g) was treated with 80 mL of liquid anhydrous ammonia chilled to −78° C. The mixture was sealed in a pressure vessel and warmed to 26° C. for 22.5 hours. The excess ammonia was evaporated to give a solid. The solid was recrystallized from 5 mL hot dimethylformamide and water; crystallization was initiated by cooling the solution in an ice bath. The solid was filtered, washed (water) and vacuum dried (100° C., 15 Pa) to give the title compound (0.274 g); mp 344.5°–346.4° C. (dec); NMR: 11.47 (s,1), 8.10 (d,1, J=8.7), 7.53 (d,1, J=2.0), 7.27 (dd,1, J=8.7, 2.0), 7.1 (broad s,2, $NH_2$), 6.23 (s,1).

Analysis for $C_{10}H_7ClN_2O_2$: Calculated: C, 53.95; H, 3.17; N, 12.58; Found: C, 53.80; H, 3.34; N, 12.89.

The intermediate 8-chloro-3-methoxy-2,5-dioxo-2,5-dihydro-1H-benz[b]azepine was prepared as follows.

a. 4-(4-Chlorophenyl)butyric acid. 3-(4-Chlorobenzoyl)propionic acid (49.94 g) was dissolved in triethylene glycol (320 mL).

To the stirred solution was added potassium hydroxide (44.5 g) followed by 98% hydrazine hydrate (29.0 g). The mixture was heated to reflux (142° C.) for 2 hours. Water and hydrazine hydrate were distilled at atmospheric pressure; the pot temperature rose to 195°–200 C. After 0.5 hour at 195°–200° C., the mixture was cooled to ambient temperature and diluted with water (320 mL). The aqueous solution was poured into 6N hydrochloric acid (200 mL) and further diluted with 200 mL of ice water. Upon standing, a solid formed which was filtered, washed (water) and dried under vacuum (25° C., 15 Pa) to afford the acid as a white solid (43.61 g).

b. 7-Chloro-1-tetralone 4-(4-Chlorophenyl)butyric acid (26.62 g) was added to 150 g of hot polyphosphoric acid (90° C.); the mixture was maintained at 90°–95° C. for 0.33 hour. After cooling to room temperature, the reaction mixture was added to 400 mL of ice-cold stirred water. The solution was allowed to warm to room temperature; and the resulting precipitate was filtered, washed (water) and air dried to give a pale yellow solid (22.3 g). The solid was recrystallized from toluene (50 mL) at −10° C. The crystals were collected and washed with cold toluene and then hexanes to give the tetralone as pale yellow crystals (18.18 g); mp 100.3°–101.1° C.

c. 7-Chloro-2-hydroxy-1,4-naphthoquinone.

7-Chloro-1-tetralone (27.56 g) was dissolved in 445 mL dry tert-butanol and added over a one hour period to a solution of freshly sublimed potassium tert-butoxide (102.7 g) in tert-butanol (1.15 L) saturated with oxygen. Oxygen was bubbled through the solution for two hours after completion of the addition. The mixture was poured into stirred ice cold 2N hydrochloric acid (1.9 L) and extracted with diethyl ether. The ethereal extracts were evaporated to give a yellow solid, which was triturated with ethyl acetate. The solid was filtered, washed (water) and dried under vacuum (25° C., 15 Pa). A portion of the yellow solid (10.5 g) was then taken up in hot ethyl acetate (0.5 L) and the solution was concentrated to 50 mL. Crystallization was initiated by cooling the solution in an ice bath. The solid was filtered, washed (cold ethyl acetate and hexane) and dried under vacuum (25° C., 15 Pa), to give yellow plates (7.10 g); mp 215°–216.5° C.

Alternatively, the intermediate 7-chloro-2-hydroxy-1,4-naphthoquinone can be prepared from 7-chloro-1-tetralone using the following procedure.

A 1-liter 4-neck flask, equipped with thermometer, medium frit gas diffusion inlet tube with in-line antisuckback trap, 250 mL addition funnel, and magnetic stirring, was charged with dry dimethylformamide (75 mL) and 0.5M potassium bis(trimethylsilyl)amide (KHMDS) in toluene (222 mL, 111 mmol). The stirred pale yellow solution was cooled to 5° C., the introduction of gaseous oxygen was begun at a rate of 70 to 100 mL/minute, and 7-chloro-1-tetralone (10 g) dissolved in dry dimethylformamide (125 mL) was added dropwise at a rate such that the reaction temperature was held below 15° C. with the aid of external ice bath cooling. The addition required about 30 minutes. Oxygen addition was continued until the starting material was consumed (about 1.5 hour) as determined by TLC (eluent 3:1 chloroform:methanol); samples for TLC spotting were prepared by acidifying several drops of reaction mixture to about pH 1 with 2N hydrochloric acid and extracting with ethyl acetate. During the reaction period the mixture gradually became bright red in color, and red solid began to separate out. At the end of the reaction period, the mixture was checked for the presence of peroxides using enzyme (peroxidase) catalyzed, redox indicator test paper. The mixture was quenched with ice cold 4N hydrochloric acid (250 mL), and the resulting yellow mixture was stirred for 30 minutes. The bright yellow product was filtered and the filter cake washed with ether and dried to afford the naphthoquinone (5.47 g). The filtrate was placed in a separatory funnel; and the organic layer was separated, dried and evaporated. The residue was triturated with ether. Additional product separated and was filtered and dried (1.14 g).

d. 7-Chloro-2-methoxy-1,4-naphthoquinone

7-Chloro-2-hydroxy-1,4-naphthoquinone (0.73 g) was added to 4% (w/w) hydrogen chloride in methanol (14 mL). The solution was heated to reflux for 0.5 hour. Upon cooling to room temperature, a precipitate formed which was filtered, washed (methanol) and dried under vacuum (25° C., 15 Pa) to give an orange solid (0.72 g); 250 MHz NMR: 8.10 (d,1, J=2.2), 8.04 (d,1, J=8.3), 7.71 (dd,1, J=8.3, 2.2), 6.19 (s,1), 3.92 (s,3).

e. 8-Chloro-3-methoxy-2,5-dioxo-2,5-dihydro-1H-benz[b]azepine

7-Chloro-2-methoxy-1,4-naphthoquinone (0.71 g) was added to concentrated sulfuric acid (4.1 mL) chilled in an ice bath. The cold red solution was stirred under nitrogen, and sodium azide (0.23 g) was added. The reaction mixture was maintained in an ice bath for 0.33 hour and was then allowed to warm to room temperature for 18 hours. The reaction mixture was cooled in an ice bath, and an additional portion of sodium azide (0.21 g) was added. After 0.33 hour the mixture was allowed to warm to room temperature for 20 hours. The mixture was cooled in an ice bath, and sodium azide (0.21 g) was added; the mixture was maintained in an ice bath for 0.33 hour and then at room temperature for 68 hours. The reaction mixture was then poured into ice cold saturated aqueous sodium bicarbonate (200 mL). The resulting precipitate was filtered, washed (water) and dried under vacuum (25° C., 15 Pa) to give a dark solid. The solid was recrystallized from dimethylformamide (3 mL) and water (1 mL) to give the benz[b]azepine as a white solid (0.2 g); 250 MHz NMR: 11.39 (s,1, NH), 7.93 (d,1, J=8.8), 7.47 (d,1, J=1.7), 7.28 (dd,1, J=8.8, 1.7) 6.35 (s,1), 3.80 (s,3).

Alternatively, the 8-chloro-3-methoxy-2,5-dioxo-2,5-dihydro-1H-benz[b]azepine can be prepared from 7-chloro-2-methoxy-1,4-naphthoquinone using the following procedure.

7-Chloro-2-methoxy-1,4-naphthoquinone (14.74 g) was added to trifluoromethanesulfonic acid (153 mL) chilled in an ice bath, and sodium azide (4.74 g) was added. The reaction mixture was maintained in an ice bath for 0.33 hour then allowed to warm to room temperature and maintained thus for 90 hours. The reaction mixture was recooled in an ice bath, and an additional portion of sodium azide (2.15 g) was added. After 0.08 hour the mixture was allowed to warm to room temperature for 19 hours. The reaction mixture was then poured into ice cold aqueous sodium bicarbonate (2.3 L). The resulting precipitate was filtered, washed (water) and dried under vacuum (25° C., 15 Pa) to give a tan solid (13.83 g). The solid was recrystallized from hot dimethylformamide (300 mL) and dried under vacuum (25° C., 15 Pa) to give the benz[b]azepine as a light tan solid (8.12 g); mp 340°–342° C. (dec). Analysis for $C_{11}H_8ClNO_3$: Calculated: C, 55.60; H, 3.39; N, 5.89; Found: C, 55.35; H, 3.38; N, 6.07.

Example 2

3-Amino-2,5-dioxo-2,5-dihydro-1H-benz[b]azepine 2,5-Dihydro-2,5-dioxo-3-methoxy-1H-benz[b]azepine (0.4 g) was treated with 80 mL of liquid anhydrous ammonia chilled to −78° C. The mixture was sealed in a pressure vessel and warmed to 23° C. for 18 hours. The excess ammonia was evaporated to give a solid. The solid was dissolved in hot methanol (120 mL); the solution was filtered and evaporated to 60 mL; and crystallization was initiated by cooling the solution in an ice bath. The solid was filtered, washed (cold methanol) and dried under vacuum (25° C., 15 Pa) to give the title compound (0.28 g); mp 295.2°–296.5° C. (dec); NMR: 11.38 (s,1, NH), 8.09 (dd,1, J=8.2, 1.6), 7.54 (m,1), 7.44 (dd,1, J=8.2, 1.6), 7.21 (m,1), 6.23 (s,1). Analysis for $C_{10}H_8N_2O_2$: Calculated: C, 63.82; H, 4.28; N, 14.89; Found: C, 63.80; H, 4.41; N, 14.87.

The starting 3-methoxy benz[b]azepine intermediate can be prepared as described in UK patent specification 1 340 334.

Examples 3–5

Using a procedure similar to that described in Example 1, the following compounds of Formula I, wherein $R^1$, $R^2$, $R^4$ and $R^8$ are each hydrogen, and $R^3$ and the group $NR^6R^7$ have the indicated values, were prepared from the corresponding compounds of Formula II wherein $R^5$ is methyl and the required amine, with exceptions as noted.

Example 3

$R^3$=chloro, $NR^6R^7$=methylamino

Allowed to react for 1 day. Recrystallized from methanol to give the title compound; NMR: 5.74 (s,1); MS: m/z=237 (M+1). Analysis for $C_{11}H_9ClN_2O_2$: Calculated: C, 55.83; H, 3.83; N, 11.84; Found: C, 55.81; H, 3.85; N, 11.89.

Example 4

$R^3$=hydrogen, $NR^6R^7$=methylamino

Allowed to react for 12 hours. Recrystallized from methanol to give the title compound; NMR: 5.75 (s,1); MS: m/z=203(M+1). Analysis for $C_{11}H_{10}N_2O_2$: Calculated: C, 65.33; H, 4.98; N, 13.85; Found: C, 65.18; H, 4.87; N, 13.78.

Example 5

$R^3$=chloro, $NR^6R^7$=dimethylamino

Allowed to react for 4 days. Recrystallized from dimethylformamide and water to give the title compound; NMR: 5.66 (s,1); MS: m/z=251(M+1). Analysis for $C_{12}H_{11}ClN_2O_2$: Calculated: C, 57.50; H, 4.42; N, 11.17; Found: C, 57.27; H, 4.46; N, 11.01.

Example 6

8-Chloro-2,5-dioxo-3-phenethylamino-2,5-dihydro-1H-benz[b]azepine

8-Chloro-3-methoxy-2,5-dioxo-2,5-dihydro-1H-benz[b]azepine (0.5 g) was treated with 5 mL of phenethylamine, and the mixture was heated to 80° C. for 1 hour. The reaction mixture was filtered and the solid recrystallized from 5 mL hot dimethylformamide and water. The solid was filtered, washed (water) and vacuum dried (100° C., 15 Pa) to give the title compound (0.329 g); mp 284.4°–286.9° C.; NMR: 5.89 (s,1); MS: m/z=327(M+1). Analysis for $C_{18}H_{15}ClN_2O_2 \cdot 0.2\ H_2O$: Calculated: C, 65.44; H, 4.70; N, 8.48; Found: C, 65.42; H, 4.72; N, 8.62.

Examples 7–18

Using a procedure similar to that described in Example 6, the following compounds of Formula I, wherein $R^1$, $R^2$, $R^4$, and $R^8$ are each hydrogen, $R^3$ is chloro and the group $NR^6R^7$ has the indicated value, were prepared from 8-chloro-3-methoxy-2,5-dioxo-2,5-dihydro-1H-benz[b]azepine and the required amine, with exceptions as noted.

Example 7

$NR^6R^7$=morpholino

Recrystallized from dimethylformamide and water; NMR: 6.00 (s,1); MS: m/z=293(M+1). Analysis for $C_{14}H_{13}ClN_2O_3 \cdot 0.2\ H_2O$: Calculated: C, 56.75; H, 4.56; N, 9.45; Found: C, 56.87; H, 4.40; N, 9.63.

Example 8

$NR^6R^7$=allylamino

Heated to 80° C. for 2 hours and recrystallized from dimethylformamide and water; NMR: 5.79 (s,1); MS: m/z=263(M+1). Analysis for $C_{13}H_{14}ClN_2O_2 \cdot 0.2\ H2O$: Calculated: C, 58.63; H, 4.31; N, 10.52; Found: C, 58.68; H, 4.28; N, 10.53.

Example 9

$NR^6R^7$=(S)-α-methylbenzylamino

Heated to 80° C. for 1 day and recrystallized from ethyl acetate; NMR: 5.67 (s,1); MS: m/z=327(M+1). Analysis for

Example 10

NR⁶R⁷=tert-butoxycarbonylmethylamino

Heated to 80° C. for 11 hours and recrystallized from dimethylformamide; NMR: 5.73 (s,1); MS: m/z=337(M+1). Analysis for $C_{16}H_{17}ClN_2O_4$: Calculated: C, 57.06; H, 5.09; N, 8.32; Found: C, 56.79; H, 5.07; N, 8.31.

Example 11

NR⁶R⁷=1-perhydroazepinyl

Heated to 80° C. for 3 hours and recrystallized from dimethylformamide and water; NMR: 5.67 (s,1); MS: m/z=305(M+1). Analysis for $C_{16}H_{17}ClN_2O_2$: Calculated: C, 63.05; H, 5.62; N, 9.19; Found: C, 62.98; H, 5.64; N, 9.13.

Example 12

NR⁶R⁷=1-pyrrolidinyl

Heated to 85° C. for 5 hours and recrystallized from dimethylformamide and water; NMR: 5.60 (s,1); MS: m/z=277(M+1). Analysis for $C_{14}H_{13}ClN_2O_2$: Calculated: C, 60.77; H, 4.731 N, 10.12; Found: C, 60.67; H, 4.80; N, 10.11.

Example 13

NR⁶R⁷=anilino

Heated to 150° C. for 1 day and recrystallized from dimethylformamide and water; NMR: 6.24 (s,1); MS: m/z=299(M+1). Analysis for $C_{16}H_{11}ClN_2O_2$: Calculated: C, 64.33; H, 3.71; N, 9.38; Found: C, 61.89; H, 3.71; N, 9.01.

Example 14

NR⁶R⁷=4-phenylpiperazin-1-yl

Heated to 80°C. for 1 day and recrystallized from dimethylformamide and water; NMR: 6.04 (s,1); MS: m/z=368 (M+1). Analysis for $C_{20}H_{18}ClN_3O_2 \cdot 0.2\ H_2O$: Calculated: C, 64.67; H, 4.99; N, 11.31; Found: C, 64.71; H, 5.00; N, 11.53

Example 15

NR⁶R⁷=4-benzylpiperazin-1-yl

Heated to 80° C. for 10.5 hours and recrystallized from dimethylformamide and water; NMR: 5.98 (s,1); MS: m/z=382(M+1). Analysis for $C_{21}H_{20}ClN_3O_2 \cdot 0.1\ H_2O$: Calculated: C, 65.71; H, 5.78; N, 10.95; Found: C, 65.40; H, 5.43; N, 10.85.

Example 16

NR⁶R⁷=piperidino

Heated to 80° C. for 1.5 hours and recrystallized from ethanol and water; NMR: 5.93 (s,1); MS: m/z=291(M+1). Analysis for $C_{15}H_{15}ClN_2O_2 \cdot 0.5\ H_2O$: Calculated: C, 60.10; H, 5.38; N, 9.34; Found: C, 60.08; H, 5.31; N, 9.28.

Example 17

NR⁶R⁷=(R)-α-methylbenzylamino

Heated to 100° C. for 1 day and recrystallized from ethanol; NMR: 5.67 (s,1); MS: m/z=327(M+1). Analysis for $C_{18}H_{15}ClN_2O_2 \cdot 0.2\ H_2O$: Calculated: C, 65.43 H, 4.70; N, 8.48; Found: C, 65.50; H, 4.50; N, 8.46.

Example 18

NR⁶R⁷=2-(N,N-dimethylamino)ethylamino

Heated to 80° C. for 1 hour and recrystallized from ethanol; NMR: 5.86 (s,1); MS: m/z=294(M+1). Analysis for $C_{14}H_{16}ClN_3O_2$: Calculated: C, 57.24; H, 5.49; N, 14.30; Found: C, 56.96; H, 5.49; N, 14.20.

Example 19

8-Chloro-3-(D-glucamino)-2,5-dioxo-2,5-dihydro-1H-benz[b]azepine

To a stirred solution of 8-chloro-3-methoxy-2,5-dioxo-2,5-dihydro-1H-benz[b]azepine (0.5 g) in dimethylformamide (15 mL) was added D-glucamine (1.9 g). The mixture was heated to 80° C. for 1 hour, cooled to 24° C. and filtered. The solid was recrystallized from 150 mL hot ethanol and water, filtered, washed (water) and vacuum dried (100° C., 15 Pa) to give the title compound (0.254 g); mp 270°–270.2° C.: NMR: 5.90 (s,1); MS: m/z=387(M+1). Analysis for $C_{16}H_{19}ClN_2O_7$: Calculated: C, 49.69; H, 4.95; N, 7.24; Found: C, 49.30; H, 4.91; N, 7.17.

Example 20

8-Chloro-2,5-dioxo-3-(4-phenoxypiperidino)-2,5-dihydroxy-1H-benz[b]azepine

A procedure similar to that described in Example 19 was used, except 4-phenoxypiperidine was substituted for (D)-glucamine and the crude material was purified by chromatography, with hexanes:ethyl acetate (1:1) as the eluent, to obtain the title compound: NMR: 6.02 (s,1); MS: m/z=383(M+1). Analysis for $C_{21}H_{19}ClN_2O_3 \cdot 0.2\ H_2O$: Calculated: C, 65.27; H, 5.06; N, 7.25; Found: C, 65.12; H, 5.12; N, 7.15.

Example 21

3-Benzylamino-8-chloro-2,5-dioxo-2,5-dihydro-1H-benz[b]azepine

To a stirred solution of 8-chloro-3-methoxy-2,5-dioxo-2,5-dihydro-1H-benz[b]azepine (0.5 g) in methanol (15 mL) was added benzylamine (0.3 mL). The mixture was heated to reflux for 24 hours. The solvent was evaporated to give a solid. The solid was recrystallized from dimethylformamide (5 mL) and water, washed (water) and vacuum dried (100° C., 15 Pa) to give the title compound (0.181 g); mp 309.1°–313.9° C.; NMR: 5.73 (s,1); MS: m/z=313(M+1). Analysis for $C_{17}H_{13}ClN_2O_2$: Calculated: C, 65.29; H, 4.19; N, 8.96; Found: C, 65.02; H, 3.96; N, 8.61.

Examples 22–24

Using a procedure similar to that described in Example 21, the following compounds of Formula I, wherein $R^1$, $R^2$, $R^4$ and $R^8$ are each hydrogen, $R^3$ is chloro and the group NR⁶R⁷ has the indicated value, were prepared from 8-chloro-2,5-dioxo-3-methoxy-2,5-dihydro-1H-benz[b]azepine and the required amine, with exceptions as noted.

Example 22

NR⁶R⁷=cyclopropylmethylamino

Heated to 65° C. for 4.5 hours and recrystallized from dimethylformamide and water; NMR: 5.88 (s,1); MS: m/z=277(M+1). Analysis for $C_{14}H_{13}ClN_2O_2$: Calculated: C, 60.77; H, 4.73; N, 10.12; Found: C, 60.62; H, 4.89; N, 10.13.

Example 23

NR$^6$R$^7$=3,4-dibenzyloxyphenethylamino

Heated to 65°C. in the presence of triethylamine (0.3 mL) for 1.5 days and recrystallized from dimethylformamide and water; NMR: 5.89 (s,1); MS: m/z=539(M+1). Analysis for C$_{32}$H$_{21}$ClN$_2$O$_4$: Calculated: C, 71.30; H, 5.05; N, 5.20; Found: C, 70.87; H, 5.13; N, 5.33.

Example 24

NR$^6$R$^7$=2-(4-imidazolyl)ethylamino

Heated to 65° C. in the presence of triethylamine (7.6 mL) for 1.5 days and recrystallized from dimethylformamide and water; NMR: 5.87 (s,1); MS: m/z=317(M+1). Analysis for C$_{15}$H$_{13}$ClN$_4$O$_2$: Calculated: C, 56.70; H, 4.44; N, 17.63; Found: C, 56.72; H, 4.28; N, 17.49.

Example 25

3-(D-Glucamino)-2,5-dioxo-2,5-dihydro-1H-benz[b]azepine

Using a procedure similar to that described in Example 21, except substituting D-glucamine for the benzylamine, and 3-methoxy-2,5-dioxo-2,5-dihydro-1H-benz[b]azepine for the 8-chloro-2,5-dioxo-3-methoxy-2,5-dihydro-1H-benz[b]azepine used therein and purifying by recrystallization from ethanol and water, the title compound was prepared; NMR: 5.90 (s,1); MS: m/z=353(M+1). Analysis for C$_{16}$H$_{20}$N$_2$O$_7$: Calculated: C, 54.54; H, 5.72; N, 7.95; Found: C, 54.51; H, 5.74; N, 7.89.

Example 26

3-Anilino-2,5-dioxo-2,5-dihydro-1H-benz[b]azepine

3-Methoxy-2,5-dioxo-2,5-dihydro-1H-benz[b]azepine (1.0 g) and aniline (10 mL) were heated to reflux for 5 hours and diluted with water. Hydrochloric acid (2N) was added and the mixture extracted with ethyl acetate. The organic extracts were washed (acid, brine), dried and evaporated to give a solid which was purified by chromatography, with ethyl acetate:toluene (1:4) as the eluent. Recrystallization from ethyl acetate gave the title compound (0.405 g); mp 227°–228° C.: NMR: 6.28 (s,1); MS(EI): m/z=264(M). Analysis for C$_{16}$H$_{12}$N$_2$O$_2$.0.1 H$_2$O : Calculated: C, 72.22; H, 4.62; N, 10.53; Found: C, 72.32; H, 4.68; N, 10.65.

Examples 27

3-Benzylamino-2,5-dioxo-2,5-dihydro-1H-benz[b]azepine

Using a procedure similar to that described in Example 26, except substituting benzylamine for the aniline used therein, the title compound was prepared; NMR: 5.73 (s,1); MS(EI): m/z=278(M). Analysis for C$_{17}$H$_{14}$N$_2$O$_2$: Calculated: C, 73.37; H, 5.07; N, 10.01; Found: C, 73.37; H, 5.22; N, 9.78.

Example 28

B 3-[N,N-bis(2-Hydroxyethyl)amino]-2,5-dioxo-2,5-dihydro-1H-benz[b]azepine

3-Methoxy-2,5-dioxo-2,5-dihydro-1H-benz[b]azepine (1.0 g) was treated with diethanolamine (10 mL), and the mixture was heated to 140° C. for 2 hours. The mixture was diluted with water and extracted with ethyl acetate. The combined organic extracts were washed with brine, dried and evaporated. The solid was recrystallized from ethanol to give the title compound (53 mg); mp 204°–205° C.; NMR: 5.90 (s,1); MS: m/z=277(M+1). Analysis for C$_{14}$H$_{16}$NO$_4$: Calculated: C, 60.80; H, 5.84; N, 10.14; Found: C, 61.29; H, 5.29; N, 11.74.

Example 29

3-[N-(2-hydroxyethyl)amino]-2,5-dioxo-2,5-dihydro-1H-benz[b]azepine

To a solution of 3-methoxy-2,5-dioxo-2,5-dihydro-1H-benz[b]azepine (1.0 g) in methanol (20 mL) was added ethanolamine (0.36 g). The mixture was heated to reflux until a precipitate formed. The reaction mixture was cooled to room temperature, filtered, and the resulting solid was recrystallized from ethanol to give the title compound (0.72 g); mp 207° C.; NMR: 5.91 (s,1); MS(EI): m/z=232(M). Analysis for C$_{12}$H$_{12}$N$_2$O$_3$.0.2 H$_2$O : Calculated: C, 61.11; H, 5.30; N, 11.88; Found: C, 61.13; H, 5.20; N, 11.72.

Example 30

3-tert-Butoxycarbonlmethylamino-2,5-dioxo-2,5-dihydro-1H-benz[b]azepine

Using a procedure similar to that described in Example 29, except substituting 3-tert-butoxycarbonylmethylamine for the ethanolamine used therein, the title compound was prepared; NMR: 5.73 (s,1); MS: m/z=303(M+1). Analysis for C$_{16}$H$_{18}$N$_2$O$_4$.0.1 H$_2$O: Calculated: C, 63.19; H, 6.03; N, 9.21; Found: C, 62.97; H, 5.94; N, 9.20.

Example 31

4-Benzyl-3-hydroxy-2,5-dioxo-2,5-dihydro-1H-benz[b]azepine

To a solution of 4-benzyl-3-methoxy-2,5-dioxo-2,5-dihydro-1H-benz[b]azepine (0.45 g) in dichloromethane was added boron tri-bromide (4.6 mL). Upon completion of the reaction, the mixture was added to ice water and extracted with ethyl acetate. The combined organic extracts were washed with brine, dried and evaporated. The resulting solid was recrystallized from toluene to give the title compound (0.336 g); mp 199°–200° C.; NMR: 3.97 (s,2); MS(EI): m/z=279(M). Analysis for C$_{17}$H$_{13}$NO$_3$.0.1 H$_2$O: Calculated: C, 72.64; H, 4.73; N, 4.98; Found: C, 72.65; H, 4.59; N, 4.94.

The intermediate 4-benzyl-3-methoxy-2,5-dioxo-2,5-dihydro-1H-benz[b]azepine was prepared as described in Example 39.

Example 32

3-Hydroxy-4-methyl-2,5-dioxo-2,5-dihydro-1H-benz[b]azepine

To a solution of 3-methoxy-4-methyl-2,5-dioxo-2,5-dihydro-1H-benz[b]azepine (0.47 g) in dichloromethane was added boron tri-bromide (6.5 mL). The precipitate which formed was diluted with water and extracted with ethyl acetate. The combined organic extracts were washed with brine, dried and evaporated. The solid was recrystallized from hot toluene to give the title compound (0.31 g); mp 252.3° C.; NMR: 2.07 (s,3); MS(EI): m/z=203(M). Analysis for C$_{11}$H$_9$NO$_3$.0.2 H$_2$O: Calculated: C, 63.89; H, 4.58; N, 6.77; Found: C, 63.79; H, 4.49; N, 6.73.

The intermediate 3-methoxy-4-methyl-2,5-dioxo-2,5-dihydro-1H-benz[b]azepine was prepared as described in Example 40.

Example 33

3-Hydroxy-4-(4-methoxycarbonyl)benzyl-2,5-dioxo-2,5-dihydro-1H-benz[b]azepine To a solution of 3-methoxy-4-(4-methoxycarbonyl) benzyl-2,5-dioxo-2,5-dihydro-1H-benz[b]azepine (0.35 g) in dichloromethane was added boron tribromide (3 mL). After 2 hours the mixture was diluted with water and extracted with ethyl acetate. The combined organic extracts were washed with brine, dried and evaporated to give the title compound (0.06 g); mp 285°–290° C.; NMR: 4.03 (s,2); MS: m/z=324(M+1). Analysis for $C_{18}H_{13}NO_5 \cdot 0.2\ H_2O$: Calculated: C, 66.13; H, 4.13; N, 4.28; Found: C, 66.09; H, 4.23; N, 4.29.

The intermediate 3-methoxy-4-(4-methoxycarbonyl) benzyl-2,5-dioxo-2,5-dihydro-1H-benz[b]azepine was prepared as described in Example 41.

Example 34

8-Chloro-4-iodo-3-methoxy-2,5-dioxo-2,5-dihydro-1H-benz[b]azepine

To a suspension of 8-chloro-3-methoxy-2,5-dioxo-2,5-dihydro-1H-benz[b]azepine (3.00 g) in glacial acetic acid (250 mL) was added sodium acetate (2.07 g) followed by iodine monochloride (15.2 mL). The mixture was heated to reflux for 1.5 hours, was allowed to cool, and the acetic acid was evaporated from the reaction mixture. The solid residue was suspended in tetrahydrofuran and stirred for 15 minutes. The solution was filtered and the resulting filtrate evaporated. The yellowish solid was recrystallized from refluxing toluene (700 mL) to afford the title compound (3.8 g); 250 MHz NMR: 11.60 (broad s, 1), 7.59 (d,1, J=7.1), 7.30 (d,1, J=1.4), 7.23 (dd,1, J=7.1, 1.6), 3.90 (s,3). Analysis for $C_{11}H_7ClINO_3$: Calculated: C, 36.34; H, 1.94; N, 3.85; Found: C, 36.35, H, 1.87; N, 3.82.

Example 35

8-Chloro-3-hydroxy-4-methyl-2,5-dioxo-2,5-dihydro-1H-benz[b]azepine

8-Chloro-4-iodo-3-methoxy-2,5-dioxo-2,5-dihydro-1H-benz[b]azepine (0.50 g) was suspended in toluene (12 mL) and trans-benzyl(chloro)bis(triphenylphosphine)palladium (II) (50 mg) and tetramethyltin (0.30 mL) were added. The mixture was allowed to reflux for 17 hours, was cooled to room temperature, and 10% (w/w) aqueous potassium fluoride (3 mL) was added, followed by 3N hydrochloric acid (10 mL). The resulting mixture was warmed to 50° C. for 6 hours. The reaction mixture was filtered, and the crude product was washed (water, hexane). Crystallization, twice, from dimethylformamide and water gave the title compound as an off-white solid (110 mg); mp 277°–279° C.; NMR: 11.72 (s,1), 10.28 (s,1), 7.95 (d,1, J=8.7), 7.48 (t,1, J=2.0), 7.31 (dd,1, J=8.7, 2.0), 2.07 (s,1). Analysis for $C_{11}H_8ClNO_3 \cdot 0.10\ H_2O$: Calculated: C, 55.18; H, 3.45; N, 5.85; Found: C, 55.23; H, 3.47; N, 5.83.

Example 36

8-Chloro-3-diethylamino-2,5-dihydro-2,5-dioxo-1H-benz[b]azepine

8-Chloro-4-iodo-3-methoxy-2,5-dioxo-2,5-dihydro-1H-benz[b]azepine (0.4 g) was treated with diethylamine (20 mL). The mixture was sealed in a pressure vessel and heated to 60° C. for 17 hours. The reaction mixture was concentrated to a brown solid which was recrystallized from hot ethyl acetate. The solid was filtered, washed and air dried to give the title compound as a yellow solid; NMR: 5.70 (s,1); MS: m/z=279(M+1).

Example 37

8-Chloro-2,5-dioxo-3-pyrrolo-2,5-dihydro-1H-benz[b]azepine

To a solution of 3-amino-8-chloro-2,5-dioxo-2,5-dihydro-1H-benz[b]azepine (0.5 g) in glacial acetic acid (5 mL) was added dropwise 2,5-dimethoxy tetrahydrofuran (0.3 mL) over 10 minutes. The mixture was heated to reflux for 12 hours. The reaction mixture was filtered and the solid recrystallized from dimethylformamide and water to give the title compound; mp 250.3°–250.7° C.; NMR: 6.24 (s,1); MS: m/z=273(M+1). Analysis for $C_{14}H_9ClN_2O_2$: Calculated: C, 61.66; H, 3.33; N, 10.27; Found: C, 62.04; H, 3.54; N, 9.85.

Example 38

8-Chloro-3-dimethylamino-4-methyl-2,5-dioxo-2,5-dihydro-1H-benz[b]azepine

8-Chloro-3-methoxy-4-methyl-2,5-dioxo-2,5-dihydro-1H-benz[b]azepine (0.4 g) was treated with 100 mL of liquid dimethylamine chilled to −78° C. The mixture was sealed in a pressure vessel and warmed to 26° C. for 72 hours. The excess dimethylamine was evaporated to give an oil which was dissolved in water and extracted with ethyl acetate. The organic extracts were combined and concentrated to a brown oil. The oil was crystallized using ether to give a yellow solid. The solid was purified by chromatography, with ethyl acetate:hexane (1:1) as the eluent, to give the title compound; NMR: 2.95 (s,6), 2.28 (s,3); MS: m/z=265(M+1).

The intermediate 8-chloro-3-methoxy-4-methyl-2,5-dioxo-2,5-dihydro-1H-benz[b]azepine was prepared as described in Example 42.

Example 39

4-Benzyl-3-methoxy-2,5-dioxo-2,5-dihydro-1H-benz[b]azepine

To diisopropylamine (0.5 g) in dry tetrahydrofuran (5 mL) at −70° C. was added butyllithium (2.1 mL, 2.5M in hexanes). The mixture was warmed to 0° C. and added to a suspension of 3-methoxy-2,5-dioxo-2,5-dihydro-1H-benz[b]azepine (0.5 g) in dry tetrahydrofuran (5 mL) at −70° C. The mixture was warmed to −50° C. for 1 hour. Benzyl bromide (351 mL) was added, and the mixture was warmed to room temperature for 17 hours. The mixture was diluted with water, acidified with 2N hydrochloric acid and extracted with ethyl acetate. The combined organic extracts were washed with brine, dried and evaporated. The solid was purified by chromatography, with ethyl acetate:toluene (1:4) as the eluent, to give a yellow solid (0.258 g); NMR: 4.07 (s,2); MS(EI): m/z=293(M).

The 4-benzyl compound also was prepared from 4-bromo-3-methoxy-2,5-dioxo-2,5-dihydro-1H-benz[b]azepine by treatment of a solution in tetrahydrofuran at −78° C. with two equivalents of butyl lithium, followed by treatment with benzyl bromide using a method similar to that described above.

Example 40

3-Methoxy-4-methyl-2,5-dioxo-2,5-dihydro-1H-benz[b]azepine

3-Methoxy-2,5-dioxo-2,5-dihydro-1H-benz[b]azepine (0.5 g) and anhydrous lithium chloride (0.63 g) were added to dry tetrahydrofuran (10 mL), and the mixture was cooled to −70° C. To this was added diisopropylamine (380 mL), followed by butyllithium (2.2 mL, 2.5M in hexanes); and the mixture was warmed to −20° C. After 30 minutes, methyl iodide (307 mL) was added and the mixture cooled to −10° C. for 10 minutes. The mixture was diluted with water, acidified with 2N hydrochloric acid and extracted with ethyl acetate. The combined organic extracts were washed with brine, dried and evaporated. The solid was purified by chromatography, with ethyl acetate:toluene (1:1) as the eluent, and recrystallized from hot toluene to give the methylated product as a white solid (0.367 g); NMR: 2.03 (s,3); MS(EI): m/z=217(M).

Example 41

3-Methoxy-4-(4-methoxycarbonyl)benzyl-2,5-dioxo-2,5-dihydro-1H-benz[b]azepine

A solution of 3-methoxy-2,5-dioxo-2,5-dihydro-1H-benz[b]azepine (10 g), lithium chloride (12.5 g) and diisopropylamine (7.5 mL) in tetrahydrofuran (200 mL) was cooled to −70° C.; and butyllithium (2.5M in hexanes, 43 mL) was added, maintaining the temperature below −60° C. The mixture was warmed to 20° C. for 1 hour, and cooled to −70° C. A portion of the resulting 2,5-dihydro-2,5-dioxo-1,4-dilithio-3-methoxy-1H-benz[b]azepine solution (0.188M in tetrahydrofuran, 26 mL) was added to a solution of methyl 4-bromomethylbenzoate (2.2 g) was dissolved in tetrahydrofuran (15 mL) and cooled to −70° C. The mixture was warmed to room temperature, diluted with water, acidified with 2N hydrochloric acid and extracted with ethyl acetate. The combined organic extracts were washed with brine, dried and evaporated. The solid was purified by chromatography, with ethyl acetate:toluene (1:3) as the eluent, to give the 4-(4-methoxycarbonyl)benzyl compound; NMR: 3.95 (s,2); MS: m/z=352(M+1).

Example 42

8-Chloro-3-methoxy-4-methyl-2,5-dioxo-2,5-dihydro-1H-benz[b]azepine

Trifurylphosphine (72 mg) was added to a toluene (150 mL) solution of tris(dibenzylideneacetone)dipalladium(0) (72 mg) at 25° C. The initial red color changed to yellow after 15 minutes of stirring. 8-Chloro-4-iodo-3-methoxy-2,5-dioxo-2,5-dihydro-1H-benz[b]azepine (3.5 g) was added to the yellow solution, followed by tetramethyltin (1.5 mL). The mixture was heated to reflux and after 5 hours cooled to 30° C. and palladium catalyst and trifurylphosphine added in equal amounts (70 mg). The mixture was reheated to reflux for 17 hours. Two more additions of catalyst were needed before the reaction was complete. The reaction mixture darkened to a green black color. The reaction mixture was filtered and the filtrate treated with 1M aqueous potassium fluoride (60 mL). The solution was filtered through a cake of diatomaceous earth and the layers separated. The organic layer was evaporated to a solid which was purified by chromatography, using ethyl acetate:hexane (3:2) as the eluent, to give a yellow solid which was recrystallized from hot toluene to give 8-chloro-3-methoxy-4-methyl-2,5-dioxo-2,5-dihydro-1H-benz[b]azepine as a yellow solid; NMR: 3.81 (s,3), 2.04 (s,3); MS: m/z=252(M+1).

Example 43

The following illustrate representative pharmaceutical dosage forms containing a compound of formula I or of formula II, for example as illustrated in any of the previous Examples, (hereafter referred to as "Compound X"), for therapeutic or prophylactic use in humans:

|  | mg/tablet |
|---|---|
| (a) Tablet | |
| Compound X | 50.0 |
| Mannitol, USP | 223.75 |
| Croscarmellose sodium | 6.0 |
| Maize starch | 15.0 |
| Hydroxypropylmethylcellulose (HPMC), USP | 2.25 |
| Magnesium stearate | 3.0 |
| (b) Capsule | |
| Compound X | 10.0 |
| Mannitol, USP | 488.5 |
| Croscarmellose sodium | 15.0 |
| Magnesium stearate | 1.5 |

(c) Injection

A sterile aqueous solution for intravenous administration may be prepared by dissolving the "Compound" in distilled water containing hydroxypropylmethylcellulose (0.5% by weight) and Tween 80 (0.1% by weight). Thus, for example, an aqueous solution having the following composition may be prepared:

| Compound X | 3.5 g/l |
|---|---|
| Hydroxypropylmethylcellulose (HPMC), USP | 1.0 g/l |
| Tween 80 (polyoxyethylene sorbitan monooleate) | 5.0 g/l |

The above formulations may be obtained by conventional procedures well known in the pharmaceutical art. The tablets may be enteric coated by conventional means, for example, to provide a coating of cellulose acetate phthalate. The injectable solutions may be prepared using typical manufacturing procedures for parenteral products, for example by using sonication as required to help effect dissolution of the "Compound".

Formulae

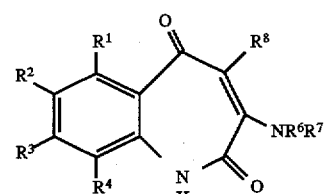

I

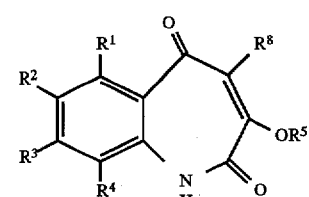

II

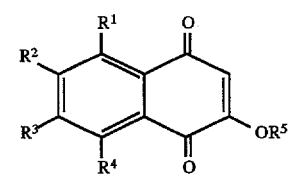

III

-continued
Formulae
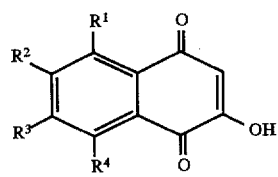   IV
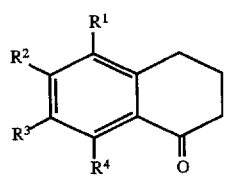   V
-continued
Formulae
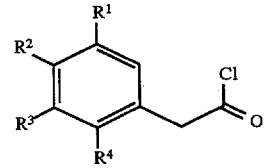   VIa
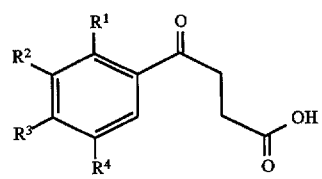   VII
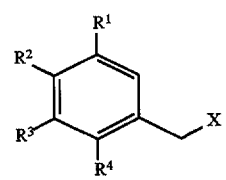   VIII
Scheme I
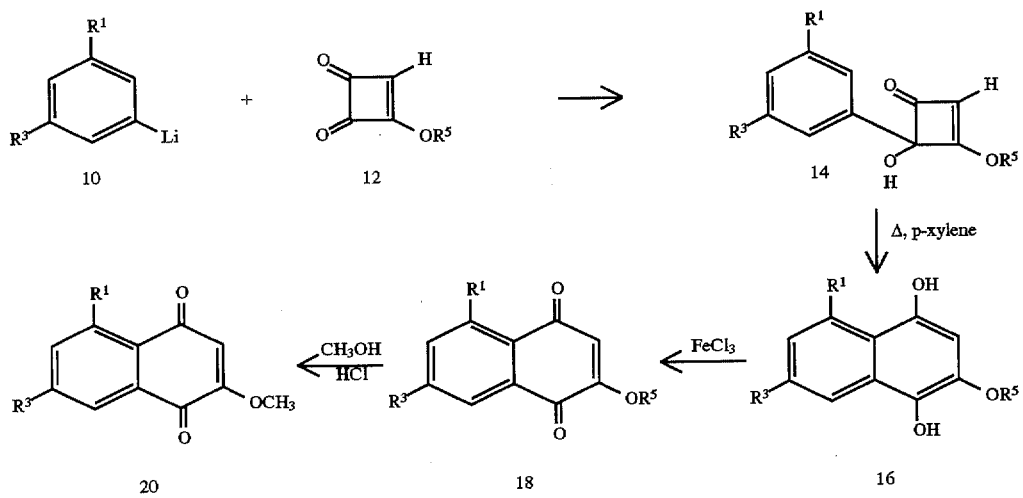
-continued
Formulae
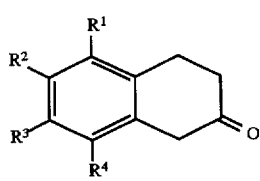   Va
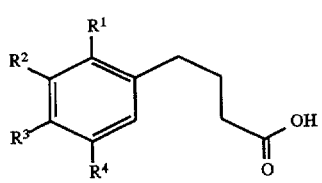   VI
What we claim is:
1. A method for the treatment of neurological disorders, comprising administering to a mammal in need of such treatment an effective amount of a compound of formula I or a compound of formula II,
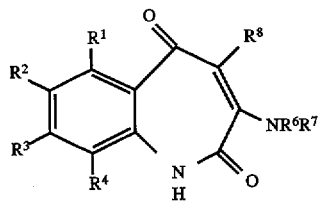   I -continued

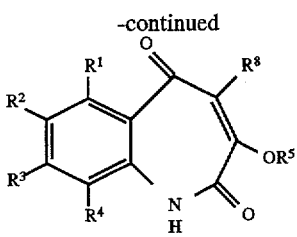
II wherein

R¹, R², R³ and R⁴ are independently selected from hydrogen, (1–3C)perfluoroalkyl, halo, nitro and cyano;

R⁵ is selected from hydrogen and (1–6C)alkyl;

R⁶ and R⁷ are independently selected from hydrogen, (1–6C)alkyl, (2–6C)alkenyl, (3–7C)cycloalkyl, (3–7C) cycloalkyl(1–6C)alkyl, aryl, aryl(1–6C)alkyl, heteroaryl, heteroaryl(1–6C)alkyl and $CH_2Y$ wherein Y is selected from $(CHOH)_nCH_2OH$ and $(CH_2)_mR^c$ wherein m is 0 to 5, n is 1 to 5 and $R^c$ is selected from hydroxy, (1–6C)alkoxy, (1–6C)alkoxycarbonyl, carboxy, and $NR^dR^e$ in which $R^d$ and $R^e$ are independently selected from hydrogen and (1–4C)alkyl or $R^d$ and $R^e$, together with the nitrogen atom to which they are attached, form a saturated 5-, 6- or 7-membered heterocyclic ring which optionally contains one additional heteroatom selected from nitrogen, oxygen and sulfur; or R⁶ and R⁷, together with the nitrogen atom to which they are attached, form a 5-, 6- or 7-membered heterocyclic ring which is bonded to said compound through said nitrogen atom, said heterocyclic ring optionally containing one additional heteroatom selected from nitrogen, oxygen and sulfur, and wherein said heterocyclic ring may be substituted with 0–2 substituents selected from (1–6C)alkyl, phenyl, phenyl (1–4C)alkyl, phenoxy and phenyl(1–4C)alkoxy;

R⁸ is selected from hydrogen, halo, (1–6C)alkyl which may optionally bear a substituent selected from amino, (1–6C)acylamino, carboxy and carboxamido, aryl (1–6C)alkyl and heteroaryl(1–6C)alkyl;

and wherein each aryl moiety is selected from phenyl and naphthyl; each heteroaryl moiety is selected from 5- and 6-membered aromatic rings containing up to 3 heteroatoms independently selected from oxygen, sulfur, and nitrogen; and wherein each aryl or heteroaryl moiety may be substituted with 0–2 substituents selected from halo, cyano, hydroxy, carboxy, nitro, (1–6C)alkyl, (1–6C)alkoxy, (2–6C)alkenyl, phenyl, phenyl(1–4C)alkyl, phenoxy, phenyl(1–4C)alkoxy and (1–6C)alkoxycarbonyl;

or a pharmaceutically acceptable salt thereof; provided that in compounds of formula II, R⁸ is not hydrogen; and excluding the compound of formula II in which R¹–R⁴ are each hydrogen, R⁸ is bromo and R⁵ is hydrogen and its pharmaceutically acceptable salt.

2. A method as claimed in claim 1 wherein the compound is of formula I and R⁶ and R⁷ are independently selected from hydrogen, (1–6C)alkyl, (3–7C)cycloalkyl(1–6C)alkyl, aryl, aryl(1–6C)alkyl, and heteroaryl(1–6C)alkyl and $CH_2Y$ wherein Y is selected from $(CHOH)_nCH_2OH$ and $(CH_2)_mR^c$ wherein m is 0 to 5, n is 1 to 5 and $R^c$ is selected from hydroxy, (1–6C)alkoxycarbonyl and $NR^dR^e$ in which $R^d$ and $R^e$ are independently selected from (1–4C)alkyl, or R⁶ and R⁷, together with the nitrogen atom to which they are attached, form a 5-, 6- or 7-membered heterocyclic ring which is bound to said compound through said nitrogen atom, said heterocyclic ring optionally containing one additional heteroatom selected from nitrogen, oxygen and sulphur and wherein said heterocyclic ring may be substituted with 0–2 substituents selected from (1–6C)alkyl, phenyl, phenyl(1–4C)alkyl, phenoxy and phenyl(1–4C)alkoxy; and wherein an aryl or heteroaryl moiety may be substituted with 0–2 substitutes selected from halo, cyano, hydroxy, carboxy, nitro, (1–6C)alkyl, (1–6C)alkoxy, (2–6C)alkenyl, phenyl, phenyl(1–4C)alkyl, phenoxy, phenyl(1–4C)alkoxy and (1–6C)alkoxycarbonyl.

3. A method as claimed in claim 1 wherein:

R¹, R², R³ and R⁴ are independently selected from hydrogen and halo;

R⁵ is hydrogen or methyl;

R⁶ is selected from hydrogen, (1–6C)alkyl, aryl, aryl (1–6C)alkyl and $CH_2Y$ wherein Y is selected from $(CHOH)_nCH_2OH$ and $(CH_2)_mR^c$ wherein m is 0 to 5, n is 1 to 5 and $R^c$ is (1–6C)alkoxycarbonyl; and R⁷, is hydrogen or (1–6C)alkyl; or R⁶ and R⁷, together with the nitrogen atom to which they are attached from a 5-, 6- or 7-membered heterocyclic ring which is bound to said compound through nitrogen atom, and wherein said heterocyclic ring is selected from morpholino, imidazolyl, pyrrolidinyl, pyrrolo, pyrazolyl, piperidinyl [which may optionally bear a 4-substituent selected from (1–6C)alkyl, phenyl(1–6C)alkyl, phenoxy and phenyl], 4-morpholinyl, piperazinyl [which may optionally bear a 4-substituent selected from (1–6C) alkyl, phenyl(1–6C)alkyl and phenyl] and perhydroazepinyl; and wherein an aryl is a phenyl and wherein an aryl or heteroaryl moiety may be substituted with 0–2 substituents selected from halo, hydroxy, carboxy, nitro, (1–6C)alkyl, (1–6C)alkoxy, (2–6C) alkenyl, phenyl, phenyl(1–4C)alkyl, phenoxy, phenyl (1–4C)alkoxy and (1–6C)alkoxycarbonyl; and R⁸ is hydrogen, (1–6C)alkyl or iodo.

4. A method as claimed in claim 1 wherein:

R¹, R² and R⁴ are each hydrogen;

R³ is hydrogen or chloro;

R⁵ is selected from hydrogen and methyl;

the group —NR⁶R⁷ is selected from: amino, methylamino, dimethylamino, diethylamino, phenethylamino, 4-morpholino, allylamino, 1-methylbenzylamino, t-butoxycarbonylmethylamino, 1-perhydroazepinyl, α-pyrrolidinyl, anilino, pyrrolo, 4-phenylpiperazin-1-yl, 4-benzylpiperazin-1-yl, piperidino, 2-(N,N-diethylamino)ethylamino, glucamino, 4-phenoxypiperadino, benzylamino, cyclopropylmethylamino, 3,4-dibenzyloxyphenethylamino, 2-(4-imidazolyl) ethylamino, N,N-bis(2-hydroxyethyl)amino, and N-(2-hydroxyethyl)amino; R⁸ is selected from hydrogen, benzyl, methyl, 4-methoxycarbonylbenzyl and iodo.

5. A method as claimed in claim 1 wherein the compound is of formula II and R⁵ is hydrogen.

6. A method for the treatment of neurological disorders, comprising administering to a mammal in need of such treatment an effective amount of a compound of formula I, wherein:

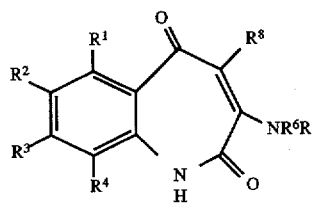

R¹, R², R³ and R⁴ are independently selected from:
hydrogen, (1-3C)perfluoroalkyl, halo, nitro and cyano;
R⁶ and R⁷ are independently selected from hydrogen, CH₂Y wherein Y is selected from (CH₂)ₘOH and (CHOH)ₙCH₂OH wherein m is 0 to 5 and n is 1 to 5,
aryl, and aryl(1-6C)alkyl wherein each aryl moiety is selected from phenyl and naphthyl each of which may be substituted with 0-2 substituents selected from halo, cyano hydroxyl, nitro, (1-6C)alkyl, (1-6C)alkoxy, vinyl, and allyl; and
heteroaryl, and heteroaryl(1-6C)alkyl wherein each heteroaryl moiety is selected from 5- and 6-membered aromatic rings containing up to 3 heteroatoms independently selected from oxygen, sulfur, and nitrogen;
or R⁶ and R⁷, together with the nitrogen atom to which they are attached, form a 5-, 6- or 7-membered heterocyclic ring which is bonded to said compound through said nitrogen atom, said heterocyclic ring optionally containing one additional heteroatom selected from nitrogen, oxygen and sulfur;
R⁸ is selected from hydrogen,
(1-6C)alkyl which may optionally bear a substituent selected from amino, (1-6C)acylamino, carboxy, and carboxamido; and
aryl(1-6C)alkyl;
or a pharmaceutically acceptable salt thereof.

7. A pharmaceutical composition comprising a compound of formula I or of formula II,

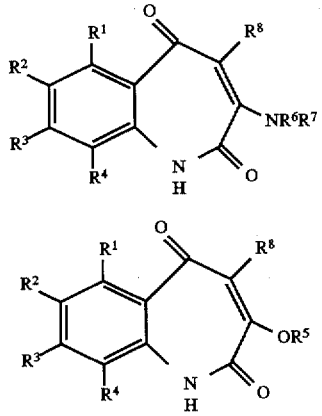

wherein

R¹, R², R³ and R⁴ are independently selected from hydrogen, (1-3C)perfluoroalkyl, halo, nitro and cyano;

R⁵ is selected from hydrogen and (1-6C)alkyl;

R⁶ and R⁷ are independently selected from hydrogen, (1-6C)alkyl, (2-6C)alkenyl, (3-7C)cycloalkyl, (3-7C)cycloalkyl, aryl, aryl(1-6C)alkyl, heteroaryl, heteroaryl(1-6C)alkyl and CH₂Y wherein Y is selected from (CHOH)ₙCH₂OH and (CH₂)ₘRᶜ wherein m is 0 to 5 n is 1 to 5 and Rᶜ is selected from hydroxy, (1-6C)alkoxy, (1-6C)alkoxycarbonyl, carboxy, and NRᵈRᵉ in which Rᵈ and Rᵉ are independently selected from hydrogen and (1-4C)alkyl or Rᵈ and Rᵉ, together with the nitrogen atom to which they are attached, form a saturated 5-, 6- or 7-membered heterocyclic ring which optionally contains one additional heteroatom selected from nitro, oxygen and sulfur; or R⁶ and R⁷, together with the nitrogen atom to which they are attached, form a 5-, 6- or 7-membered heterocyclic ring which is bonded to said compound through said nitrogen atom, said heterocyclic ring optionally containing one additional heteroatom selected from nitrogen, oxygen and sulfur, and wherein said heterocyclic ring may be substituted with 0-2 substituents selected from (1-6C)alkyl, phenyl, phenyl(1-4C)alkyl, phenoxy and phenyl(1-4C)alkoxy;

R⁸ is selected from hydrogen, halo (1-6C)alkyl which may optionally bear a substituent selected from amino, (1-6C)acylamino, carboxy and carboxamido, aryl (1-6C)alkyl and heteroaryl(1-6C)alkyl;

and wherein each moiety is selected from phenyl and naphthyl; each heteroaryl moiety is selected from 5- and 6-membered aromatic rings containing up to 3 heteroatoms independently selected from oxygen, sulfur, and nitrogen; and wherein each aryl or heteroaryl moiety be substituted with 0-2 substituents selected from halo, cyano, hydroxy, carboxy, nitro, (1-6C)alkoxy, (1-6C)alkenyl, phenyl, phenyl(1-4C) alkyl, phenoxy, phenyl(1-4C)alkoxy and (1-6C) alkoxycarbonyl;

or a pharmaceutically acceptable salt thereof, and a pharmaceutically acceptable diluent or carrier; provided that in compounds of formula II, R⁸ is not hydrogen; and excluding the compound of formula II in which R¹-R⁴ are each hydrogen, R⁸ is bromo and R⁵ is hydrogen and its pharmaceutically acceptable salt.

* * * * *

UNITED STATES PATENT AND TRADEMARK OFFICE
CERTIFICATE OF CORRECTION

PATENT NO. : 5,712,272
DATED : January 27, 1998
INVENTOR(S) : Harris et al.

It is certified that error appears in the above-identified patent and that said Letters Patent is hereby corrected as shown below:

In the Claims:

Column 30, line 50, "1-methylbenzylamino" should read -- α-methylbenzylamino --.

Column 30, line 51, "α-pyrrolidinyl" should read -- 1-pyrrolidinyl --.

Column 32, line 45, "alkoxy, (1-6c)alkenyl, phenyl" should read -- alkyl, (1-6c)alkoxy, (2-6c)alkenyl --.

Signed and Sealed this

Twenty-seventh Day of July, 1999

Attest:

Attesting Officer

Q. TODD DICKINSON

Acting Commissioner of Patents and Trademarks